(12) United States Patent
Tran et al.

(10) Patent No.: US 9,752,160 B2
(45) Date of Patent: Sep. 5, 2017

(54) USE OF NON-SUBTYPE B GAG PROTEINS FOR LENTIVIRAL PACKAGING

(71) Applicants: Theravectys, Villejuif (FR); Institut Pasteur, Paris (FR)

(72) Inventors: Thi-Lan Tran, Jouy en Josas (FR); Pierre Charneau, Paris (FR); Cecile Bauche, Paris (FR)

(73) Assignees: THERAVECTYS, Villejuif (FR); INSTITUT PASTEUR, Paris (FR)

( * ) Notice: Subject to any disclaimer, the term of this patent is extended or adjusted under 35 U.S.C. 154(b) by 0 days.

(21) Appl. No.: 14/346,961

(22) PCT Filed: Sep. 25, 2012

(86) PCT No.: PCT/IB2012/002363
§ 371 (c)(1),
(2) Date: Mar. 24, 2014

(87) PCT Pub. No.: WO2013/046034
PCT Pub. Date: Apr. 4, 2013

(65) Prior Publication Data
US 2014/0234908 A1   Aug. 21, 2014

(30) Foreign Application Priority Data

Sep. 26, 2011 (EP) .................................. 11306222

(51) Int. Cl.
| | | |
|---|---|---|
| *C12N 15/867* | (2006.01) | |
| *C12N 15/11* | (2006.01) | |
| *C12N 7/01* | (2006.01) | |
| *C12N 15/49* | (2006.01) | |
| *C12N 15/86* | (2006.01) | |
| *C07K 14/005* | (2006.01) | |

(52) U.S. Cl.
CPC ............ *C12N 15/86* (2013.01); *C07K 14/005* (2013.01); *C12N 2740/16043* (2013.01); *C12N 2740/16052* (2013.01); *C12N 2740/16222* (2013.01); *C12N 2800/00* (2013.01)

(58) Field of Classification Search
None
See application file for complete search history.

(56) References Cited

U.S. PATENT DOCUMENTS

| | | | |
|---|---|---|---|
| 8,153,138 B2* | 4/2012 | Sutter et al. ................ | 424/232.1 |
| 2003/0044981 A1* | 3/2003 | Marasco ................. | C40B 40/02 |
| | | | 435/456 |
| 2006/0134133 A1* | 6/2006 | Moss et al. ................ | 424/199.1 |

FOREIGN PATENT DOCUMENTS

| | | |
|---|---|---|
| WO | 9013630 | 11/1990 |
| WO | 2004087201 A2 | 10/2004 |
| WO | 2005014836 A2 | 2/2005 |
| WO | 2005027840 A2 | 3/2005 |

OTHER PUBLICATIONS

De Mareuil, Jean et al., Virology, vol. 209, pp. 649-653 (1995).
De Mareuil, Jean et al., Journal of Virology, vol. 66, No. 11, pp. 6797-6801 (1992).
Hirsch, I., et al., Virology, vol. 186, pp. 647-654 (1992).
Bruno Spire et al: "Nucleotide sequence of HIV1-NDK: a highly cytopathic strain of the human immunodeficiency virus", Gene, vol. 81, pp. 275-284, 1989.

* cited by examiner

*Primary Examiner* — Maria Marvich
(74) *Attorney, Agent, or Firm* — Whitham, Curtis & Cook, P.C.

(57) ABSTRACT

The invention encompasses a lentiviral packaging vector comprising a non-subtype B gag-pol sequence, particularly a subtype D gag-pol sequence. The invention further encompasses methods for making and using these vectors. The invention further encompasses lentiviral vector particles comprising HIV-1 non-subtype B Gag and/or Pol proteins.

13 Claims, 11 Drawing Sheets

```
P17-CladeB.FR.83.HXB2_LAI_IIIB_BRU.K03455    (1)   MGARASVLSGGELDRWEKIRLRPGGKKKYKLKHIVWASRELERFAVNPGL
                     P17-CladeD.CD.83_NDK.M27323    (1)   MGARASVLSGGKLDTWERIRLRPGGKKKKYALKHLIWASRELERFTLNPGL P17-CladeB.FR.83.HXB2_LAI_IIIB_BRU.K03455   (51)   LETSEGCRQILGQLQPSLQTGSEELRSLYNTVATLYCVHQRIEIKDTKEA
                     P17-CladeD.CD.83_NDK.M27323   (51)   LETSEGCKQIIGQLQPSIQTGSEEIRSLYNTVATLYCVHERIEVKDTKEA P17-CladeB.FR.83.HXB2_LAI_IIIB_BRU.K03455  (101)   LDKIEEEQNKSKKKAQQAAADTGHSNQVSQNY
                     P17-CladeD.CD.83_NDK.M27323  (101)   VEKMEEEQNKSKKKTQQAAADS--S-QVSQNY
```

*FIG. 7*

| | | 1 | |
|---|---|---|---|
| P17-CladeB.FR.83.HXB2_LAI_IIIB_BRU.K03455 | (1) | MGARASVLSGGELDRWEKIRLRPGGKKKYKLKHIVWASRELERFAVNPGLLETSEGCRQILGQLQPSLQTGSEEL |
| P17-B.UY.01.O1UYTRA1092.AY781126 | (1) | --ARASVLSGGELDRWEKIRLRPGGKKKYRLKHIVWASRELERFAVNPGLLETTEGCRQILGQLQPSLQTGSEEL |
| P17-CladeB.CN.05.05CNHB_dw107.DQ833416 | (1) | MGARASVLSGGQLDRWEKIRLRPGGKKKYRLKHLVWASRELERFAVNPGLLETSEGCRQILEQLQPSLQTGSEEL |
| P17-CladeB.US.x.B4522TOB8U.GQ371250 | (1) | MGARASVLSGGELDRWEKIRLRPGGKKKYKLKHIVWASRELERFAVNPGLLETSGGCRQILGQLQPSLQTGSEEL |
| P17-CladeB.ZA.03.03ZAPS045MB2.DQ396398 | (1) | MGARASVLSGGELDRWEKIRLRPGGKKKYRLKHIVWASRELERFAINPGLLETSAGCRQILGQLHPSLQTGSEEL |
| P17-CladeB.CO.01.PCM074.AY561240 | (1) | -ARASVLSGGELDRWEKIRLRPGGKKKYRLKHIVWASRELERFAVNPGLLETSEGCRQILAQLQPSLPTGSEEL |
| P17-CladeB.CY.05.CY075.FJ388916 | (1) | MGARASVLSGGELDKWEKIRLRPGGKKKYKLKHIVWASRELERFAVNPGLLETSEGCRQILGQLQLGSLQTGSEEL |
| P17-CladeB.YE.02.02YE508.AY795905 | (1) | --ARASVLSGGELDRWEKIRLRPGGKKKYKLKHIVWASRELERFAVNPGLLETSEGCIQILGQLQPSLQTGSEEL |
| P17-CladeB.US.x.X1537TOB8U.GQ371695 | (1) | MGARASVLSGGELDRWEKIRLRPGGKKKYKLKHVVWASRELERFAVNPGLLETSEGCRKILGQLQPSLQTGSEEL |
| P17-CladeB.US.02.L8124P.FJ469741 | (1) | MGARASVLSGGELDRWEKIRLRPGGKKKQYKLKHIVWASRELERFALNPGLLETSEGCRQILEQLQPSLQTGSEEI |
| P17-CladeB.CY.03.CY005.EU673412 | (1) | MGARASILSGGELDRWEKIRLRPGGKKKQYRLKHIVWASRELERFAVNPGLLETSGGCKQILAQLHPSLQTGSEEL |
| P17-CladeB.AR.04.04AR143170.DQ383750 | (1) | -ARASILSGGELDRWEKIRLRPGGKKKRYRLKHIVWASRELERFSVNPGLLETSEGCRQILRQLQPALQTGSEDF |
| P17-CladeB.AU.87.MBC925.AF042101 | (1) | MGARASVLSGGELDRWEKIRLRPRGKKKYQLKHIVWASRELERFSVNPGLLETSEGCRQILRQLQPALQTGSEDF |
| P17-CladeB.US.x.AC160T9Day1034Dom.EU616649 | (1) | MGARASVLSGGELDRWEKIRLRPGGSKKYKLKHIVWASRELERFAVNPSLLETSEGCKQILGQLQPSLQTGSEEL |
| P17-CladeB.US.x.X5597TOB8U.GQ371704 | (1) | MGARASVLSGGELDKWERIRLRPGCKKKYRLKHIVWASRELERFAVNPGLLETSEGCRQIIGQLQPSLQTGSEEL |
| P17-CladeB.AR.05.2005_03.FJ155192 | (1) | MGARASVLSGGELDKWERIRLRPGGKKKYRLKHIVWASRELERFAVNPGLLETAEGCKQILAQLHPSLQTGSEEL |
| P17-CladeB.CA.x.BCCFEHOMERHIVGAG2991.EU242048 | (1) | MGARASVLSGGELDRWEKIRLRPGGKKKYKLKHVVWASRELERFAVNPGLLETXEGCRQILEQLQPALQTGSEEL |
| P17-CladeB.AR.05.2005_11.FJ155200 | (1) | ---RASVLSGGELDRWEKIRXRQGGKKKYKLKHIVWASRELERFAVNPGLLETSGGCRQILGQLQPSLQTGSEEL |
| P17-CladeB.AU.x.4922142.AY857059 | (1) | MGARASVLSGGKLDTWERIRLRPGGKKKYALKHLIWASRELERFTLNPGLLETSEGCKQIIGQLQPSLQTGSEEI |
| P17-CladeD.CD.83.NDK.M27323 | (1) | |

FIG. 8

```
P17-CladeB.FR.83.HXB2_LAI_IIIB_BRU.K03455  (1)  MGARASVLSGGELDRWEKIRLRPGGKKKYKLKHIVWASRELERFAVNPGLLETSEGCRQILGQLQPSLQTGSEEL
P17-CladeD.CD.83.NDK.M27323                (1)  MGARASVLSGGKLDTWERIRLRPGGKKKYALKHLIWASRELERFTLNPGLLETSEGCKQIIGQLQPSIQTGSEEI
P17-CladeD.FR.x.Vis20.FJ649608             (1)  MGARASVLSGGKLDAWEKIRLRPGGKKKYKLKHIVWASRELERFALNPGLLETSEGCRQIISQLQPSLKTGSEEI
P17-CladeD.UG.02.TC025704.AY803405         (1)  MGARASVLSGGKLDEWEKIRLRPGGRKTYKLKHIVWASRELERFALNPGLLETSEGCKQIIAQLQSSIQTGSEEI
P17-CladeD.UG.99.99UGD23550.AF484485       (1)  -ARASVLSGGKLDEWEKIQLRPGGHKRYKLKHIVWASRELERFAINPGLLETSGGCRQIMGQLQPAIQTGSEEL
P17-CladeD.CM.01.01CM_0009BBY.AY371155     (1)  --ARASVLSGGKLDAWEKIRLRPGGRKRYRLKHIVWASRELERFALNPGLLETSEGCKQIISQLQPSLKTGSEEL
```

USE OF NON-SUBTYPE B GAG PROTEINS FOR LENTIVIRAL PACKAGING

BACKGROUND OF THE INVENTION

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection, in order to develop a specific immune response in their host.

Such vaccines constitute a major advance in vaccine technology (Kutzler et al., Nat Rev Genet, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (Cell, 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, Gene Ther, 14(11):847-62; He et al. 2007, Expert Rev vaccines, 6(6):913-24). Sequences generally required in cis are the long terminal repeats (LTRs) and its vicinity: the inverted repeats (IR or att sites) required for integration, the packaging sequence ψ, the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, Expert Rev vaccines, 6(6):913-24), allowing antigen presentation through the endogenous pathway.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant lentiviral vectors is based on the separation of the cis- and trans-acting sequences of the lentivirus. Efficient integration and replication in non-dividing cells requires the presence of two cis-acting sequences in the lentiviral genome, the central polypurine tract (cPPT) and the central terminal sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, Cell, 101(2) 173-85; Arhel et al., 2007, EMBO J, 26(12):3025-37).

HIV-1 lentiviral vectors have been generated based on providing the subtype B Gag, Pol, Tat and Rev proteins for packaging vectors in trans from a packaging construct (Naldini et al, PNAS 15: 11382-8 (1996); Zufferey et al, Nature Biotechnology 15:871-875, 1997); Dull et al, Journal of Virology (1997)). These studies were performed with subtype B Gag and Pol proteins. The effect of non-subtype B gag and pol sequences in a HIV-1 packaging construct was not assessed.

There are many different subtypes of HIV-1 other than subtype B. Some subtypes of HIV-1, such as C, E, and A, appear to be transmitted more efficiently than HIV-1 subtype B, which is the major subtype in the United States and Europe. Essex et al., Adv Virus Res. 1999; 53:71-88. The predominant subtype of HIV-1 that is found in the developed Western World, clade B, differs considerably from those subtypes and recombinants that exist in Africa and Asia, where the vast majority of HIV-infected persons reside. Spira et al., J. Antimicrobial Chemotherapy (2003) 51, 229-240. Thus, serious discrepancies may exist between the subtype B retrovirus encountered in North America and Europe and those viral subtypes that plague humanity on a global scale. Id. Subtype diversity may impact on modes of HIV transmission. Homosexual and intravenous drug abuse are the primary modes of transmission observed for clade B strains in Europe and the Americas. Id. In contrast, clades A, C, D and E predominate in Africa and Asia where heterosexual transmission predominates. Id. In addition, some studies suggest that AIDS progression differs as a function of infecting subtype. Id. Thus, it appears that HIV-1 subtype B is quite different than the other HIV-1 subtypes.

HIV phylogenic classifications are normally based either on nucleotide sequences derived from multiple sub genomic regions (gag, pol and env) of the same isolates, or on full-length genome sequence analysis. A phylogenic analysis of HIV-1 near-full length sequences revealed that HIV-1 subtype B was most closely related genetically to HIV subtype D (FIG. 1). Phylogenic analyses of HIV-1 Gag and Pol protein sequences also showed that HIV-1 subtype B was most closely related genetically to HIV subtype D (FIG. 2).

Nevertheless, HIV-1-NDK, a subtype D virus, is significantly more cytopathic for CD4+ lymphocytes than the HIV-1-BRU prototype, a subtype B virus. This may be due to enhanced fusogenicity and infectivity of subtype D viruses. De Mareuil et al., J. Virol. 66: 6797 (1992). Phenotypic analysis of recombinant viruses indicated that 75 amino acids from the N-terminal part of HIV-1-NDK matrix (MA) protein, together with the HIV-1-NDK envelope glycoprotein, are responsible for enhanced fusogenicity of HIV-1-NDK in CD4+ lymphocytes as well as for enhanced infectivity of HIV-1-NDK in some CD4-cell lines. Id.

There is a need in the art for lentiviral packaging constructs producing higher titers of packaged lentiviral vectors, in order to reduce injection volumes, increase dosages, reduce the cost of vaccination, and increase the number of patients that could be treated with one batch. The current invention fulfills this need.

BRIEF SUMMARY OF THE INVENTION

The gag-pol gene of subtype B of HIV-1 in a lentiviral packaging plasmid (construct p8.74) was replaced by the gag-pol gene of a subtype D HIV-1 to generate construct pThV-GP-N. The constructs were used for lentiviral vector production. Approximately 2-fold higher titers were obtained using the pThV-GP-N plasmid as compared to construct p8.74. Thus, the Gag-Pol of a subtype D virus increases the titer of lentiviral vector particles relative to a Gag-Pol of a subtype B virus.

The invention encompasses a lentiviral packaging vector comprising a subtype D gag-pol sequence, particularly from HIV-1 NDK. In a preferred embodiment, the lentiviral packaging vector comprises the nucleotide sequence of SEQ ID NO:1. In a preferred embodiment, the lentiviral packaging vector encodes the amino acid sequence of SEQ ID NO:2.

The nucleotide sequence of SEQ ID NO 1 is:

```
(SEQ ID NO 1)
atgggtgcgagagcgtcagtattaagcgggggaaaattagatacatgggaaagaattcggttac ggccaggaggaaagaaaaaatatgcactaaaacatttgatatgggcaagcagggagctagaacg atttacacttaatcctggccttttagagacatcagaaggctgtaaacaaataataggacagcta caaccatctattcaaacaggatcagaagaaattagatcattatataatacagtagcaaccctct attgtgtacatgaaaggatagaggtaaaagacaccaaagaagctgtagaaaagatggaggaaga acaaaacaaagtaagaaaaagacacagcaagcagcagctgatagcagccaggtcagccaaaat tacccctatagtgcagaacctacaggggcaaatggtacatcaggccatatcacctagaactttga acgcatgggtaaaagtaatagaagaaaaggccttcagcccggaagtaatacccatgttttcagc attatcagaaggagccaccccacaagatttaaacaccatgctaaacacagtggggggacatcaa gcagctatgcaaatgctaaaagagaccatcaatgacgaagctgcagaatgggacagattacatc cagtgcatgcagggcctgttgcaccaggccaaatgagagaaccaaggggaagtgatatagcagg aactactagtacccttcaggaacaaatagcatggatgacaagcaacccacctatcccagtagga gaaatctataaaagatggataatcctgggattaaataaaatagtaagaatgtatagccctgtca gcattttggacataagacagggaccaaaggaaccttttagagactatgtagaccggttctataa aactctaagagccgagcaagcttcacaggatgtaaaaaactggatgacagaaaccttgttggtc caaaatgcaaacccagattgtaaaactatcttaaaagcattgggaccacaggctacactagaag aaatgatgacagcatgccagggagtggggggcccggccataaagcaagagttttggctgaggc aatgagccaagtaacaggttcagctactgcagtaatgatgcagagaggcaattttaagggccca agaaaaagtattaagtgtttcaactgtggcaaggaagggcacacagcaaaaaattgcagggccc ctagaaaaagggctgttggaaatgcggaagggaaggacaccaaatgaaagattgcactgaaag acaggctaattttttagggaagatttggccttcccacaagggaaggccggggaattttcttcag agcagaccagagccaacagccccaccagcagagagcttcgggtttggggaggagataaccccct ctcagaaacaggagcagaaagacaaggaactgtatcctttagcttccctcaaatcactctttgg caacgaccctcgtcacaataaagatagggggacagctaaaggaagctctattagatacaggag cagatgatacagtattagaagaaataaatttgccaggaaaatggaagccaaaaatgatagggg aattggaggttttatcaaagtaagacagtatgatcaaatactcatagaaatctgtggatataaa gctatgggtacagtattagtaggacctacacctgtcaacataattggaagaaatttgttgaccc agattggctgcactttaaattttccaattagtcctattgaaactgtaccagtaaaattaaagcc aggaatggatggcccaaaagttaaacaatggccattgacgaagaaaaaataaaagcattaacag aaatttgtacagaaatggaaaaggaaggaaaaatttcaagaattgggcctgaaaatccatataa tactccaatatttgccataaagaaaaagacagtaccaagtggagaaaattagtagatttcaga gaacttaataagagaactcaagatttctgggaggttcaattaggaataccgcatcctgcagggc tgaaaagaaaaaatcagtaacagtactggatgtgggtgatgcatatttctcagttcccttaga tgaagattttaggaaatataccgcatttaccatacctagtataaacaatgagacaccagggatt agatatcagtacaatgtgctcccacagggatggaaaggatcaccggcaatattccaaagtagca tgacaaaaatcttagagccctttagaaaacaaaatccagaaatagttatctatcaatacatgga
```

-continued

```
tgatttgtatgtaggatctgacttagaaatagggcagcatagaacaaaaatagaggaattaaga gaacatctattgaggtggggatttaccacaccagataaaaaacatcagaaagaacctccatttc tttggatgggttatgaactccatcctgataaatggacagtacagcctataaacctgccagaaaa agaaagctggactgtcaatgatatacagaagttagtggggaaattaaactgggcaagccagatt tatgcaggaattaaagtaaagcaattatgtaaactccttaggggaaccaaagcactaacagaag tagtaccactaacagaagaagcagaattagaactggcagaaaacagggaaattctaaaagaacc agtacatggagtgtattatgacccatcaaaagacttaatagcagaactacagaaacaagggac ggccaatggacataccaaatttatcaagaaccatttaaaaatctaaaaacaggaaagtatgcaa gaacgagggtgcccacactaatgatgtaaaacaattaacagaggcagtgcaaaaaatagccac agaaagcatagtgatatggggaaagactcctaaatttaaactacccatcaaaaggaaacatgg gaaacatggtggatagagtattggcaagccacctggattcctgagtgggaatttgtcaataccc ctcctttagtaaaattatggtaccagttagagaaggaacccataataggagcagaaactttcta tgtagatggggcagctaatagagagactaaattaggaaaagcaggatatgttactgacagagga agacagaaagttgtcccttcactgacacgacaaatcagaagactgagttacaagcaattaatc tagctttacaggattcgggattagaagtaaacatagtaacagattcacaatatgcactaggaat cattcaagcacaaccagataagagtgaatcagagttagtcagtcaaataatagagcagctaata aaaaggaaaaggtttacctggcatgggtaccagcacacaaaggaattggaggaaatgaacaag tagataaattagtcagtcagggaatcaggaaagtactattttttggatggaatagataaggctca ggaagaacatgagaaatatcacaacaattggagagcaatggctagtgattttaacctaccacct gtggtagcgaaagaaatagtagctagctgtgataaatgtcagctaaaaggagaagccatgcatg gacaagtagactgtagtccaggaatatggcaattagattgtacacatctggaaggaaaagttat cctggtagcagttcatgtagccagtggctatatagaagcagaagttattccagcagaaacgggg caagaaacagcatactttctcttaaaattagcaggaagatggccagtaaaagtagtacatacag ataatggcagcaatttcaccagtgctacagttaaggccgcctgttggtgggcagggatcaaaca ggaatttggaattccctacaatccccaaagtcaaggagtagtagaatctatgaataaagaatta aagaaaattataggacaggtaagagatcaagctgaacatcttaagacagcagtacaaatggcag tatttatccacaattttaaaagaaaagggggggattggggggatacagtgcaggggaaagaataat agacataatagcaacagacatacaaactagagaattacaaaaacaaatcataaaaattcaaaat tttcgggtttattacagggacagcagagatccaatttggaaaggaccagcaaagcttctctgga aaggtgaaggggcagtagtaatacaagacaatagtgacataaaggtagtaccaagaagaaaagt aaagatcattagggattatggaaaacagatggcaggtgatgattgtgtggcaagtagacaggat gaggattaac.
```

The amino acid sequence of SEQ ID NO 2 is:

(SEQ ID NO: 2)
MGARASVLSGGKLDAWERIRLRPGGKKKYALKHLIWASRELERIALNPGLLETSEGCK

QIIGQLQPSIQTGSEELRSLYNTIATLYCVHERIEVKDTKEAVEKMEEEQNKSKKKTQQ

AAADSSQVSQNYPIVQNLQGQMVHQAISPRTLNAWVKVIEEKAFSPEVIPMFSALSEG

ATPQDLNTMLNTVGGHQAAMQMLKETINDEAAEWDRLHPVHAGPVAPGQMREPRG

SDIAGTTSTLQEQIAWMTSNPPIPVGEIYKRWIILGLNKIVRMYSPVSILDIRQGPKEPFR

DYVDRFYKTLRAEQASQDVKNWMTETLLVQNANPDCKTILKALGPQATLEEMMTACQ

-continued

```
GVGGPGHKARVLAEAMSQVTGSVTAVMMQRGNFKGPRKSIKCFNCGKEGHTAKNC

RAPRKKGCWKCGREGHQMKDCSERQANFLGKIWPSHKGRPGNFLQSRPEPTAPPA

ESFGFGEEITPSQKQEQKDKELYPLASLKSLFGNDPSSQFFREDLAFPQGKAGEFSSE

QTRANSPTSRELRVWGGDNPLSETGAEGQGTVSFSFPQITLWQRPLVTIKIGGQLKEA

LLDTGADDTVLEEMNLPGKWKPKMIGGIGGFIKVRQYDQILIEICGYKAMGTVLVGPTP

VNIIGRNLLTQIGCTLNFPISPIETVPVKLKPGMDGPKVKQWPLTEEKIKALTEICTEMEK

EGKISRIGPENPYNTPIFAIKKKDSTKWRKLVDFRELNKRTQDFWEVQLGIPHPAGLKK

KKSVTVLDVGDAYFSVPLDEDFRKYTAFTIPSINNETPGIRYQYNVLPQGWKGSPAIFQ

SSMTKILEPFRKQNPEIVIYQYMDDLYVGSDLEIGQHRTKIEELREHLLRWGFTTPDKK

HQKEPPFLWMGYELHPDKWTVQPIKLPEKESWTVNDIQKLVGKLNWASQIYAGIKVK

QLCKLLRGTKALTEVVPLTEEAELELAENREILKEPVHGVYYDPSKDLIAELQKQGDGQ

WTYQIYQEPFKNLKTGKYARTRGAHTNDVKQLTEAVQKIATESIVIWGKTPKFKLPIQK

ETWETWWIEYWQATWIPEWEFVNTPPLVKLWYQLEKEPIIGAETFYVDGAANRETKL

GKAGYVTDRGRQKVVPFTDTTNQKTELQAINLALQDSGLEVNIVTDSQYALGIIQAQPD

KSESELVSQIIEQLIKKEKVYLAWVPAHKGIGGNEQVDKLVSQGIRKVLFLDGIDKAQEE

HEKYHNNWRAMASDFNLPPVVAKEIVASCDKCQLKGEAMHGQVDCSPGIWQLDCTH

LEGKVILVAVHVASGYIEAEVIPAETGQETAYFLLKLAGRWPVKVVHTDNGSNFTSATV

KAACWWAGIKQEFGIPYNPQSQGVVESMNKELKKIIGQVRDQAEHLKTAVQMAVFIHN

FKRKGGIGGYSAGERIIDIIATDIQTRELQKQIIKIQNFRVYYRDSRDPIWKGPAKLLWKG

EGAVVIQDNSDIKVVPRRKVKIIRDYGKQMAGDDCVASRQDED.
```

The invention encompasses a lentiviral packaging vector comprising a subtype D MA sequence, particularly from HIV-1 NDK. In a preferred embodiment, the lentiviral packaging vector encodes an MA protein comprising the amino acid sequence of SEQ ID NO:3.

The amino acid sequence of SEQ ID NO 3 is:

```
                                            (SEQ ID NO 3)
MGARASVLSGGKLDTWERIRLRPGGKKKYALKHLIWASRELERFTLNPG

LLETSEGCKQIIGQLQPSIQTGSEEIRSLYNTVATLYCVHERIEVKDTK

EAVEKMEEEQNKSKKKTQQAAADSSQVSQNY.
```

Preferably, the lentiviral packaging vector encoding the HIV Gag MA protein generates at least a 1.5 fold increase, or at least a 2-fold increase, in the titer of a packaged lentiviral vector as compared to the lentiviral packaging vector encoding an HIV Gag MA protein of HIV-1 BRU, e.g., p8.74. Preferably, the lentiviral packaging vector is replication-defective and lacks a ψ site.

In a preferred embodiment, the lentiviral packaging vector encodes an HIV Gag MA protein having an amino acid at position 12 that is not a glutamic acid and an amino acid at position 15 that is not an arginine. Preferably, the lentiviral packaging vector does not have both a valine at position 46 and a leucine at position 61.

In a preferred embodiment, the amino acid at position 12 of the MA protein is a lysine. In a preferred embodiment, the amino acid at position 15 is a threonine. In a preferred embodiment, the amino acid at position 15 is an alanine. In a preferred embodiment, the amino acid at position 46 is a leucine. In a preferred embodiment, the amino acid at position 61 is an isoleucine. In a preferred embodiment, the amino acid at position 61 is a methionine.

In one embodiment, the vector does not encode a functional Env protein.

The invention also encompasses methods for making the above lentiviral packaging vectors and methods for using these lentiviral packaging vectors.

BRIEF DESCRIPTION OF THE DRAWINGS

The invention is more fully understood through reference to the drawings.

GAG and POL protein sequences were obtained from: http://www.hiv.lanl.gov/content/sequence/NEWALIGN/align.html. For each known HIV clade, one patient's (for clade B) or two patients' virus sequences were randomly chosen and GAG and POL protein sequences were compared to the reference clade B proteins (B.FR.83.HXB2_LAI_IIIB_BRU.KO3455). Alignments were performed using Vector NTI advance 11 (Invitrogen).

Figure 1:
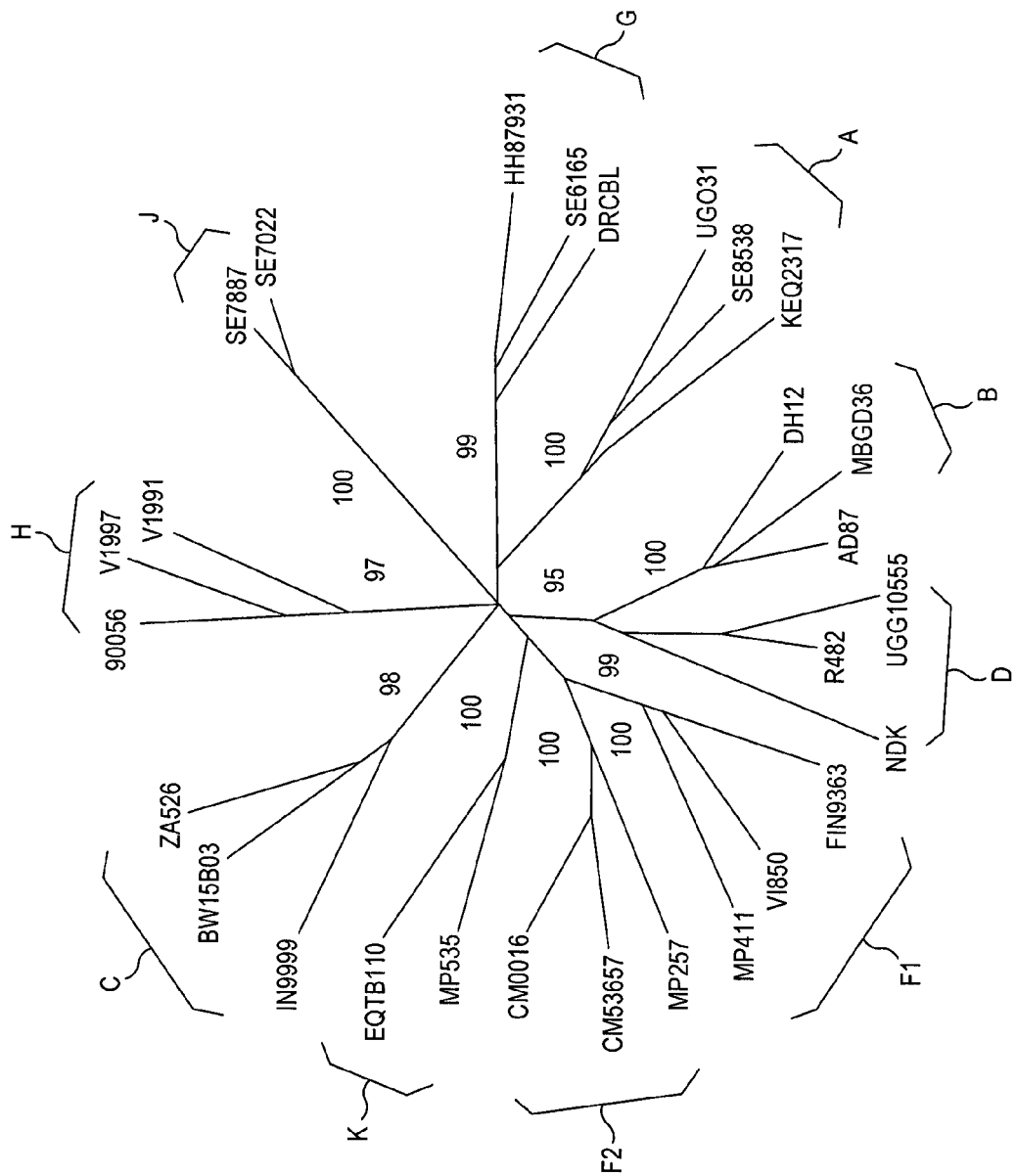
FIG. 1 depicts phylogenic trees of HIV viruses.
Figure 2:
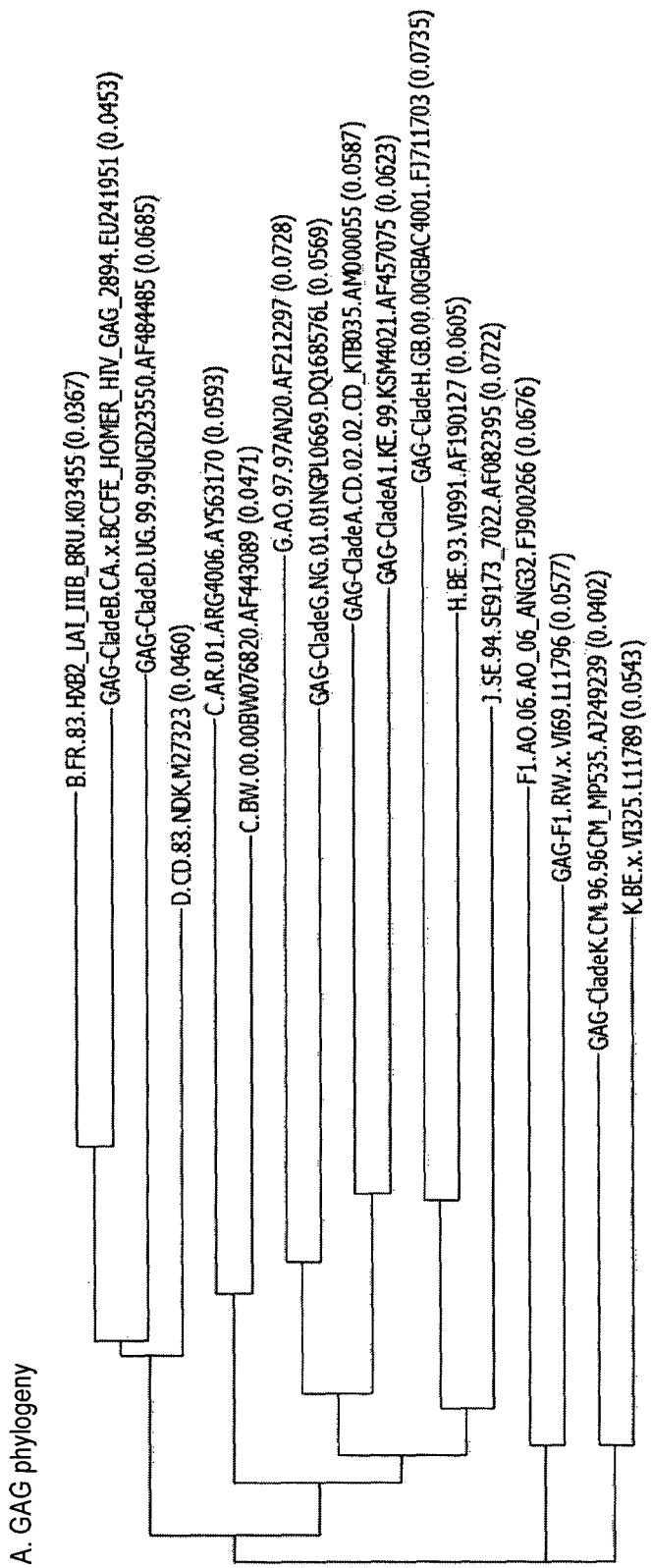
FIGS. 2A and B depict phylogenic trees of HIV GAG (A) and POL (B) proteins.
Figure 2:
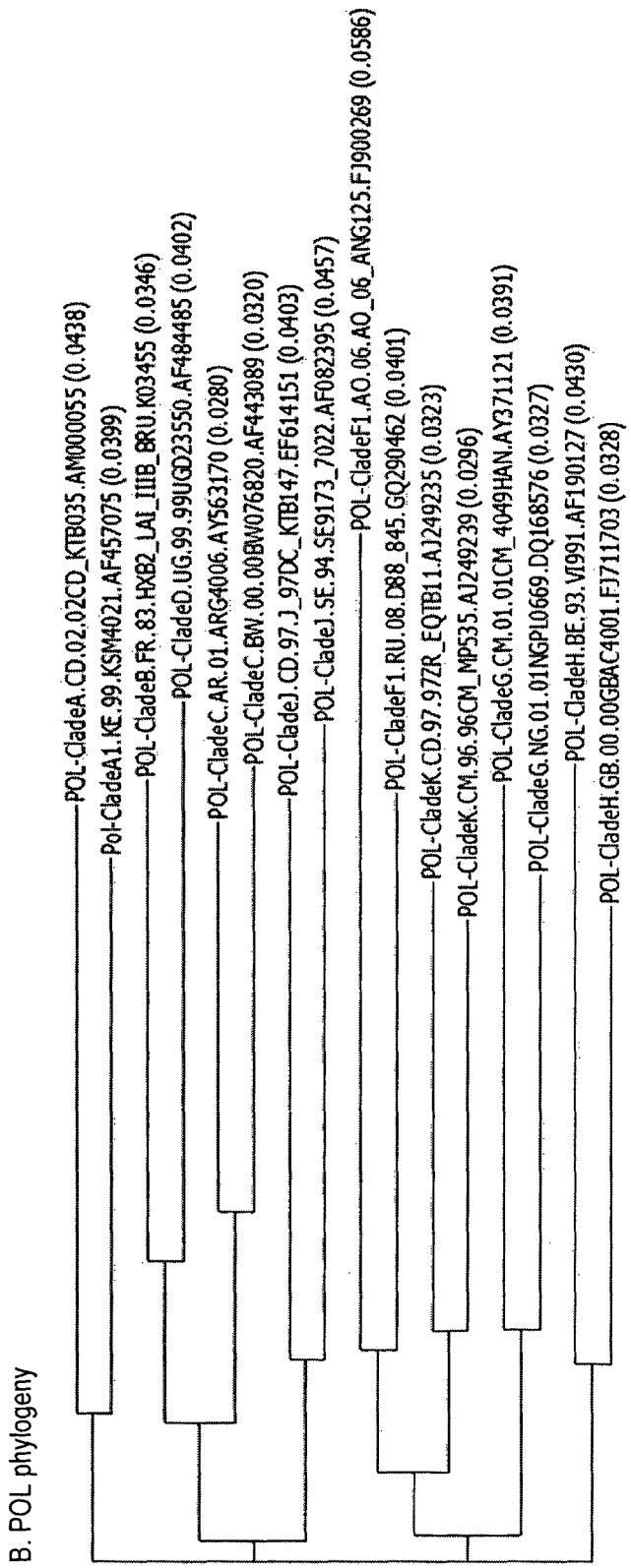
Figure 3:
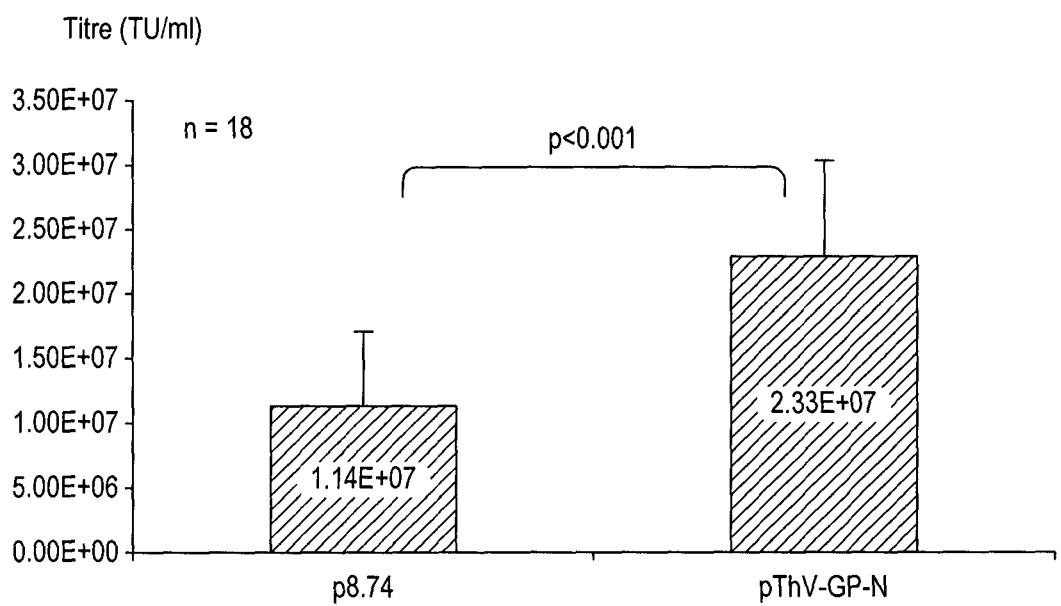

FIG. 3 depicts titers obtained using the p8.74 and the pThV-GP-N plasmids for vector production. Lentiviral particles were produced using the proviral plasmid (pFLAP-CMV-GFP), the pseudotyping plasmid (pTHV-VSV.G) and either the commonly used packaging plasmid (derived from the BRU strain, p8,74) or an NDK-derived packaging plasmid (pTHV-GP-N). With each packaging plasmid, 18 independent transfections were performed and the particles titers were measured by FACS analysis. Similar results were also obtained using a vector employing a proviral plasmid containing the β2 microglobulin promoter driving HIV antigen expression.

Figure 4A:
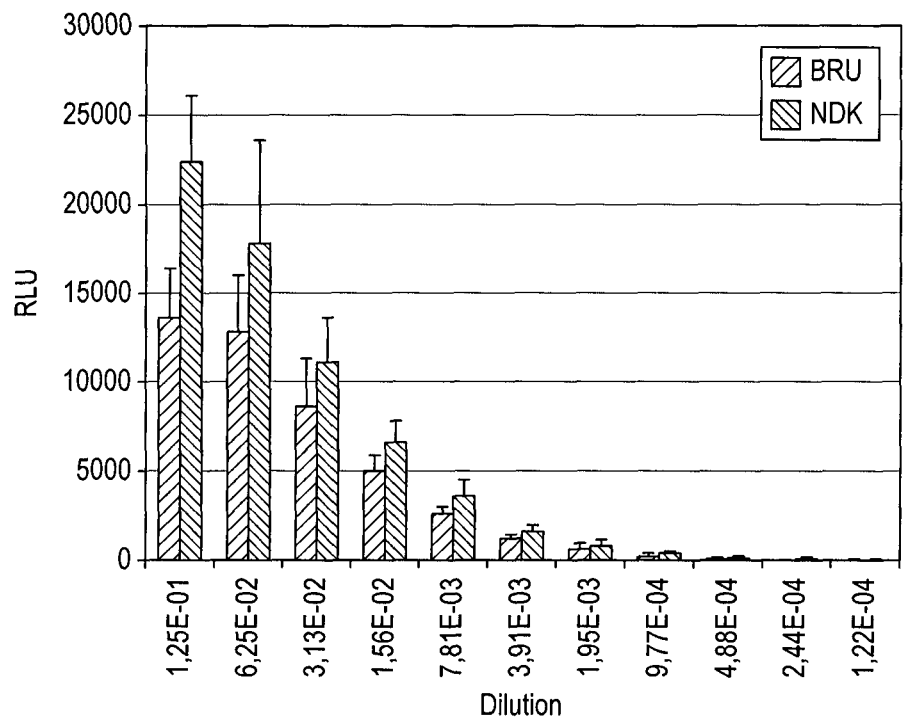
Figure 4B:
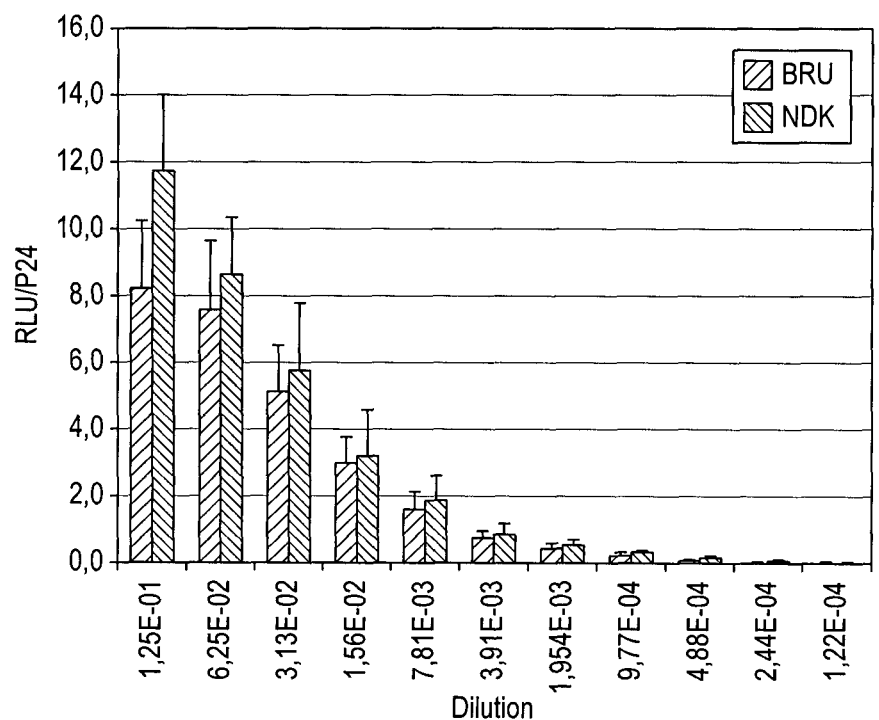

FIG. 4 depicts production of wild type BRU and NDK viruses and evaluation of their respective early phase efficiency. 293T cells were transfected either with plasmid encoding for the wild type BRU (pBRU) or NDK (pNDK-N) virus. Viral supernatants were collected after 48 hours and diluted to infect P4-CCR5 cells (encompassing a stable luciferase reporting gene which expression is driven by the HIV LTR, allowing a luciferase production in presence of the TAT protein (brought by the virus). Serial dilution of either BRU or NDK viruses were used to infect P4-CCR5 cells and the luciferase expression (A) or the luciferase/P24 ratio (B) were measured.

Figure 5:
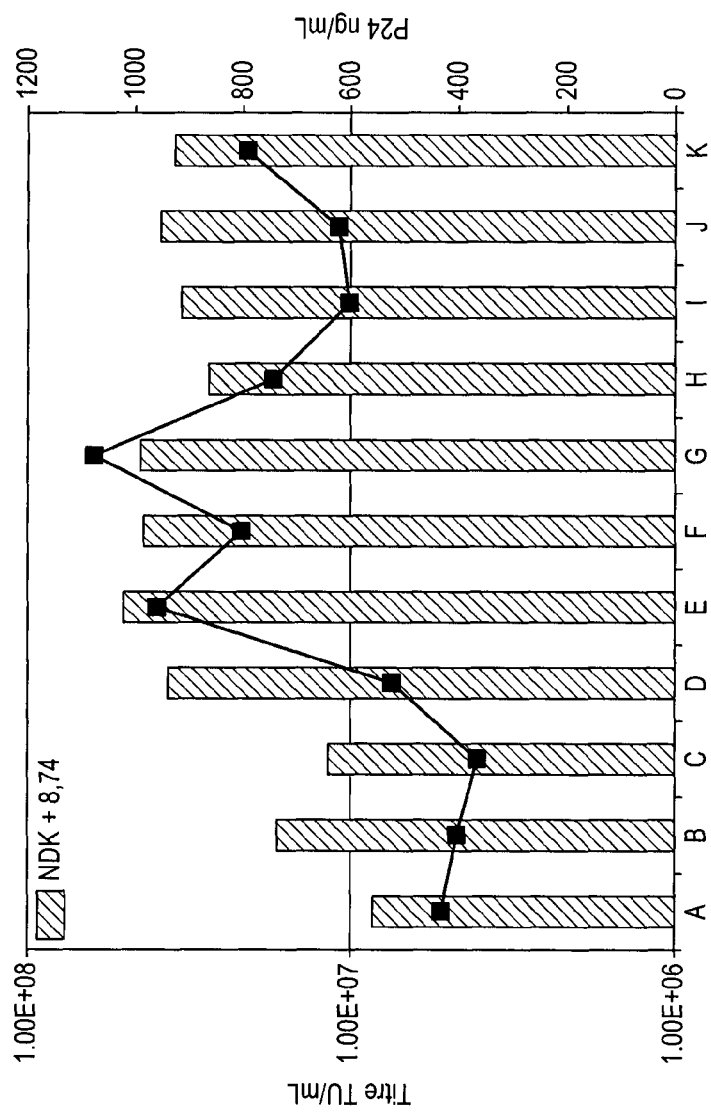

FIG. 5 depicts vector production using different ratios of BRU (p8,74) and NDK (pThV GP-N) derived packaging plasmids. For each conditions (from 0 μg NDK+10 μg BRU to 10 μg NDK+0 μg BRU), the titer (gray bars) and the P24 level (black squares) were measured.

FIG. 6 depicts a Western blot of vector supernatants produced using either BRU (8,74) or NDK (pThV GP-N) derived packaging plasmids. The P24 protein and precursors detection was performed using the NIH anti-P24 MAB (183-H12-5C).

FIG. 7 depicts a sequence alignment of the N-terminal MA sequences of a clade B virus (BRU; SEQ ID NO:5) with a clade D virus (NDK; SEQ ID NO:4).

FIG. 8 depicts a sequence alignment of the N-terminal MA sequences of clade B viruses (SEQ ID NO:6 through SEQ ID NO:26).

FIG. 9 depicts a sequence alignment of the N-terminal MA sequences of clade D viruses (SEQ ID NO:27 through SEQ ID NO:32).

FIG. 10 depicts a sequence alignment of the N-terminal MA sequences of a clade B virus (BRU) with viruses of other clades (SEQ ID NO:33 through SEQ ID NO:67).

DETAILED DESCRIPTION OF THE INVENTION

Subtype B HIV-1 viruses differ from other HIV-1 subtypes in that subtype B viruses appear to be transmitted less efficiently and have a different mode of transmission. Nevertheless, subtype B viruses have been used extensively in the generation of HIV-1 lentiviral vectors and lentiviral packaging vectors. To determine whether the Gag and Pol proteins of non-subtype B viruses could be used for the generation of lentiviral packaging vectors, the gag-pol gene of HIV-1 subtype B in a lentiviral packaging plasmid (construct p8.74) was replaced by the gag-pol gene of a subtype D HIV-1 to generate construct pThV-GP-N. The constructs were used for lentiviral vector production. Approximately 2-fold higher titers were obtained using the pThV-GP-N plasmid as compared to construct p8.74 (FIG. 3). Thus, the subtype D HIV-1 Gag-Pol in the packaging vector increased the titer of lentiviral vector over the titer seen with a subtype B HIV-1 Gag-Pol.

Increased titer of the lentiviral vector is beneficial in allowing the reduction in contaminants in a given dose of lentiviral vector. This facilitates a reduction in injection volumes, and an increase in possible dosages. It further facilitates reducing the cost of vaccination by reducing the quantity of materials and labor necessary to achieve a particular dose, and by increasing the number of patients that could be treated with a single batch of lentival vector.

Serial dilutions of HIV-1 BRU and HIV-1 NDK viruses indicated that the HIV-1 NDK virus was more efficient in the early phases of the virus life cycle (FIG. 4). By mixing different amounts of the subtype B and subtype D packaging vectors, it was demonstrated that the subtype D packaging vector increased both the titer and the level of p24 in the lentiviral vector preparations (FIG. 5). The p24 in the lentiviral vector preparations using the subtype D packaging vector was also observed to be less completely processed, showing higher levels of p24 precursors (FIG. 6). Thus, the Gag protein in the subtype D packaging vector was exhibiting various differences from the subtype B packaging vectors.

It is known that, with HIV-1 Env, the 75 amino acids from the N-terminal part of HIV-1-NDK matrix (MA) protein is responsible for enhanced fusogenicity of HIV-1-NDK in CD4+ lymphocytes as well as for enhanced infectivity of HIV-1-NDK in some CD4-cell lines. De Mareuil et al., J. Virol. 66: 6797 (1992). Since the Env protein used for generation of lentiviral vectors with the subtype B and subtype D packaging vectors is the same (i.e., VSV), only the differences in HIV-1 MA are present in the subtype B and subtype D packaging vectors.

The conservation and divergence of amino acids in the N-terminal 75 amino acids of M from various clades of HIV-1 viruses was examined. HIV-1 NDK showed 10 differences in amino acids from HIV-1 BRU (FIG. 7). However, only eight of these differences were seen when HIV-1 NDK was compared to an assortment of 20 different HIV-1 subtype B viruses (FIG. 8). When other subtype D viruses were included in the comparison, only 4 of these differences remained (FIG. 9). These differences are the absence of a glutamic acid at amino acid position 12, the absence of an arginine at amino acid position 15, the absence of a valine at amino acid position 46, and the absence of a leucine at amino acid position 61 in subtype D viruses.

When other subtype viruses were included in the comparison, the other subtypes appeared to align with subtype D, preserving nearly all of these differences (FIG. 10). Nearly all of the non-subtype B viruses exhibited a lysine at position 12. Many of the non-subtype B viruses exhibited an alanine at position 15. Nearly all of the non-subtype B viruses exhibited a leucine at position 46. Nearly all of the non-subtype B viruses exhibited a methionine or isoleucine at position 61. The non-subtype B viruses exhibited the consensus of a lysine at position 12, an amino acid other than arginine at position 15, a leucine at position 46, and an isoleucine or methionine at position 61.

The invention encompasses packaging vectors encoding non-subtype B Gag and/or Pol proteins and host cells comprising these vectors. The invention further encompasses methods for making packaging vectors encoding non-subtype B Gag and/or Pol proteins. The invention also encompasses methods for using these packaging vectors to generate lentiviral vectors, and lentiviral vectors comprising non-subtype B Gag and/or Pol proteins.

Packaging Vectors

The invention encompasses packaging vectors encoding non-subtype B Gag and/or Pol proteins. A lentiviral "packaging vector" is defined herein as a nucleic acid sequence not encoding functional HIV-1 Env and lacking a ψ site, but capable of expressing lentiviral Gag and/or Pol proteins that can be incorporated into viral particles when cotransfected with a vector containing appropriate lentiviral cis-acting signals for packaging. The lentiviral packaging vector of the invention is unable to replicate itself by packaging and reverse transcribing its own sequence.

The packaging vector can be an RNA or DNA vector. The non-subtype B Gag and Pol proteins can be selected from subtype A, subtype C, subtype D, subtype E, subtype F1, subtype F2, subtype G, subtype H, and subtype J proteins, and recombinants thereof. A preferred packaging vector comprises SEQ ID NO:1 or encodes SEQ ID NO:2.

The invention encompasses packaging vectors encoding non-subtype B Gag proteins and host cells comprising these vectors. The non-subtype B Gag proteins can be selected from subtype A, subtype C, subtype D, subtype E, subtype F1, subtype F2, subtype G, subtype H, and subtype J proteins, and recombinants thereof. A preferred packaging vector encodes the Gag protein portion of SEQ ID NO:2.

The invention encompasses packaging vectors encoding non-subtype B MA proteins and host cells comprising these vectors. The non-subtype B MA proteins can be selected from subtype A, subtype C, subtype D, subtype E, subtype F1, subtype F2, subtype G, subtype H, and subtype J proteins, and recombinants thereof. A preferred packaging vector encodes SEQ ID N0:3 or the MA protein portion of SEQ ID N0:2.

In various embodiments, the packaging vector comprises SEQ ID N0:1 or a nucleic acid sequence that is at least 95%, 96%, 97%, 98%, 99% identical with SEQ ID N0:1. In various embodiments, the packaging vector encodes SEQ ID N0:2, SEQ ID N0:3, or an amino acid sequence that is at least 95%, 96%, 97%, 98%, 99% identical with SEQ ID N0:2 or SEQ ID N0:3.

As used herein, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG), using the default parameters for the GAP program including: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

In various embodiments, the vector comprises a sequence encoding an HIV-1 MA protein having one or more of the following features:
  the absence of a glutamic acid at amino acid position 12;
  the absence of an arginine at amino acid position 15;
  the absence of a valine at amino acid position 46; and
  the absence of a leucine at amino acid position 61.

In various embodiments, the vector comprises a sequence encoding an HIV-1 MA protein having one or more of the following features:
  the amino acid at position 12 is a lysine;
  the amino acid at position 15 is a threonine;
  the amino acid at position 15 is an alanine;
  the amino acid at position 46 is a leucine;
  the amino acid at position 61 is an isoleucine; and/or
  the amino acid at position 61 is a methionine.

The packaging vector preferably encodes HIV-1 Gag and Pol. Most preferably, the packaging vector encodes an HIV-1 Gag MA protein.

The packaging vector can contain viral or non-viral sequences for expression of Gag and Pol. The packaging vector can contain an HIV-1 LTR or the U3 region of an HIV-1 LTR. In other embodiments, the packaging vector does not contain HIV-1 LTRs. Any promoter can be used to drive expression of Gag and Pol. Preferably, the promoter is a strong promoter in human cells. Most preferably, the packaging vector contains a Cytomegalovirus (CMV) promoter, a CMV early enhancer/chicken β actin (CAG) promoter, a Rous Sarcoma Virus (RSV) promoter, a human phosphoglycerate kinase (hPGK) promoter, or a U3 from an LTR (e.g., myeloproliferative sarcoma virus (MPSV) U3) promoter driving expression of the encoded genes, e.g. gag and pol.

Preferably, the packaging vector contains a polyadenylation signal. Any polyadenylation signal can be. Preferably, polyadenylation signal is a strong signal in human cells. Most preferably, the polyadenylation signal is a human α2 globin or a Bovine Growth hormone (BGH) polyadenylation signal.

Preferably, the packaging vector contains a Rev-responsive element (RRE). In a preferred embodiment, the packaging vector expresses an HIV-1 Rev protein. In a preferred embodiment, the packaging vector contains at least one splice donor site and at least one splice acceptor site. In one embodiment, the packaging vector expresses an HIV-1 Tat protein.

In preferred embodiments, the packaging vector lacks sequences encoding HIV-1 Vif, Vpr, Vpu, and/or Nef. The packaging vector can comprise a sequence encoding an HIV-1 MA protein having one or more of the features discussed herein.

In one embodiment, the packaging vector encodes only 1 HIV-1 protein, Gag. In one embodiment, the packaging vector encodes only 2 HIV-1 proteins, Gag and Pol. In one embodiment, the packaging vector encodes only 3 HIV-1 proteins, selected from Gag, Pol, Rev, and Tat. In one embodiment, the packaging vector encodes only 4 HIV-1 proteins, Gag, Pol, Rev, and Tat.

In one embodiment, the vector comprises (from 5' to 3') a CMV promoter, a nucleic acid sequence encoding HIV-1 Gag-Pol, an exon encoding part of Tat and Rev, a splice donor site, an intron containing an RRE, a splice acceptor site, an exon encoding part of Tat and Rev, and a polyadenylation signal. Preferably, the HIV-1 Gag-Pol is a subtype D HIV-1 Gag-Pol.

The packaging vector may further contain an origin for replication in bacteria or eukaryotic cells. The packaging vector may contain a selectable marker gene for selection in bacteria or eukaryotic cells.

The invention encompasses host cells comprising the packaging vectors of the invention. The host cells can be transiently transfected with the packaging vectors of the invention. The host cells can be cell lines with the packaging vectors of the invention integrated into the genome of the host cell. Many different cells are suitable host cells Preferably, the cells are human cells, most preferably an immortalized human cell line. In one embodiment, the cells are HEK 293T cells. In one embodiment, the cells are HeLA, HT1080 or PER C6 cells (Delenda et al, Cells for Gene Therapy and vector Production, from Methods in Biotechnology, Vol 24: Animal Cell Biotechnology: Methods and Protocols, $2^{nd}$ Ed. Edited by R. Portner, Humana Press Inc., Totowa, N.J.).

Packaging Systems

The invention encompasses lentiviral packaging systems comprising cells expressing non-subtype B Gag and/or Pol proteins. A lentiviral "packaging system" is defined herein as a cell-based system comprising cells expressing at least lentiviral Gag and Pol proteins in the absence of a ψ site, and capable of packaging and reverse transcribing an exogenous nucleic acid containing a ψ site. The cells of the lentiviral packaging system can also express other viral proteins. Preferably, the lentiviral packaging system expresses an envelope protein. The envelope protein can be a lentiviral (e.g., HIV-1 Env) or non-lentiviral (e.g., VSV, Sindbis virus, Rabies virus) envelope protein. In various embodiments, the lentiviral packaging system expresses an HIV-1 Tat and/or Rev protein.

In various embodiments, the cells of the lentiviral packaging system contain sequences encoding HIV-1 Gag and/or Pol stably integrated into their genome. In various embodiments, the cells of the lentiviral packaging system contain sequences encoding an envelope protein stably integrated into their genome. In various embodiments, the cells of the lentiviral packaging system contain sequences encoding HIV-1 Tat and/or Rev stably integrated into their genome.

In various embodiments, the cells of the lentiviral packaging system transiently express HIV-1 Gag and/or Pol proteins. In various embodiments, the cells of the lentiviral packaging system transiently express an envelope protein. In various embodiments, the cells of the lentiviral packaging system transiently express HIV-1 Tat and/or Rev proteins.

The cells of the lentiviral packaging system can express non-subtype B Gag and Pol proteins selected from subtype A, subtype C, subtype D, subtype E, subtype F1, subtype F2, subtype G, subtype H, and subtype J proteins, and recombinants thereof. In one embodiment, the cells of the lentiviral packaging system comprise SEQ ID NO:1 or express SEQ ID NO:2.

In various embodiments, the cells of the lentiviral packaging system express non-subtype B Gag proteins. The non-subtype B Gag proteins can be selected from subtype A, subtype C, subtype D, subtype E, subtype F1, subtype F2, subtype G, subtype H, and subtype J proteins, and recombinants thereof.

In various embodiments, the cells of the lentiviral packaging system express non-subtype B MA proteins. The non-subtype B MA proteins can be selected from subtype A, subtype C, subtype D, subtype E, subtype F1, subtype F2, subtype G, subtype H, and subtype J proteins, and recombinants thereof. A preferred packaging vector encodes SEQ ID NO:3 or the MA protein portion of SEQ ID NO:2.

In various embodiments, the cells of the lentiviral packaging system can contain any of the lentiviral vectors of the invention.

In various embodiments, the cells of the lentiviral packaging system contain SEQ ID NO:1 or a nucleic acid sequence that is at least 95%, 96%, 97%, 98%, 99% identical with SEQ ID NO:1. In various embodiments, the cells of the lentiviral packaging system express a protein with the amino acid sequence of SEQ ID NO:2, SEQ ID NO:3, or an amino acid sequence that is at least 95%, 96%, 97%, 98%, 99% identical with SEQ ID NO:2 or SEQ ID NO:3.

Methods of Producing Packaging Vectors

The invention encompasses methods for making packaging vectors encoding non-subtype B Gag and/or Pol proteins. The packaging vector can comprise any of the features discussed herein.

In one embodiment, the method comprises inserting a Gag and/or Pol sequence from a non-subtype B HIV-1 virus into a plasmid under the control of a non-HIV promoter (e.g., CMV promoter) to generate a packaging vector. In one embodiment, the packaging vector encodes only 1 HIV-1 protein. In one embodiment, the packaging vector encodes only 2 HIV-1 proteins. In one embodiment, the packaging vector encodes only 3 HIV-1 proteins, selected from Gag, Pol, Rev, and Tat. In one embodiment, the packaging vector encodes only 4 HIV-1 proteins, Gag, Pol, Rev, and Tat.

In various embodiments, the plasmid comprises one or more of a CMV promoter, an exon encoding part of Tat and Rev, a splice donor site, an intron containing an RRE, a splice acceptor site, an exon encoding part of Tat and Rev, and a polyadenylation signal.

In various embodiments, the packaging vector comprises a CMV promoter, an exon encoding part of Tat and Rev, a splice donor site, an intron containing an RRE, a splice acceptor site, an exon encoding part of Tat and Rev, and a polyadenylation signal.

The non-subtype B HIV-1 virus can be selected from subtype A, subtype C, subtype D, subtype E, subtype F1, subtype F2, subtype G, subtype H, and subtype J viruses, and recombinants thereof.

In one embodiment, the method comprises providing a packaging vector comprising a Gag sequence of an HIV-1 subtype B virus and replacing Gag sequences in the vector with sequences from an HIV-1 non-subtype B virus.

The non-subtype B HIV-1 virus can be selected from subtype A, subtype C, subtype D, subtype E, subtype F1, subtype F2, subtype G, subtype H, and subtype J viruses, and recombinants thereof. In a preferred embodiment, non-subtype B HIV-1 virus is HIV-1 NDK.

Methods of Producing Lentiviral Vectors

The invention also encompasses methods for using packaging vectors encoding HIV-1 non-subtype B Gag and/or Pol proteins to generate lentiviral vectors. In one embodiment, the invention encompasses administering a packaging vector encoding an HIV-1 non-subtype B Gag or Pol protein to a cell with a lentiviral vector. The packaging vector can comprise any of the features discussed herein.

The lentiviral vector comprises cis-acting sequences for packaging and reverse transcription, including a ψ site and primer binding site. Preferably, the lentiviral vector comprises two HIV-1 LTR sequences. In one embodiment, one of the LTRs is deleted for U3 and R sequences. Preferably, the lentiviral vector comprises a central polypurine tract (cPPT) and a central terminal sequence (CTS). The lentiviral vector preferably encodes a lentiviral or non-lentiviral protein, such as a selectable marker or tumor antigen.

In one embodiment, the lentiviral vector comprises one or more HIV antigen, preferably an HIV-1 antigen. Most preferably, the antigen is a Gag, Pol, Env, Vif, Vpr, Vpu, Nef, Tat, or Rev antigen. The antigen can be a single antigen, a mix of antigens, an antigenic polypeptide, or a mix of antigenic polypeptides from these proteins. In a preferred embodiment, the lentiviral vector comprises an HIV-1 p24 Gag antigen.

In one embodiment, the invention encompasses a lentiviral vector comprising an NIS-containing promoter. An "NIS-containing promoter" comprises an NF-Kb binding site, an interferon stimulated response element (ISRE), and an SXY module (SXY). Examples of naturally occurring NIS-containing promoters are the β2m promoter and the MHC class I gene promoters. These naturally occurring NIS-containing promoters are generally cloned or reproduced from the promoter region of a gene encoding a protein β2m or a MHC class I protein, or referred to as putatively encoding such proteins in genome databases (ex: NCBI polynucleotide database http://www.ncbi.nlm.nih.gov/guide/dna-rna). Both β2m and class I MHC proteins enter the Major Histocompatibility Complex (MHC). β2m and class I MHC promoter sequences are also usually referred to as such in genome databases—i.e. annotated as being β2m and class I MHC promoter sequences.

MHC class I and β2-microglobulin promoters contain the shared structural homologies of NIS-containing promoters.

These promoters also share the ability to be strongly activated in dendritic cells, as well as, to lower intensity, in the majority of the other human body tissues.

In one embodiment, the packaging vector and the lentiviral vector are introduced together into a cell to allow the formation of lentiviral vector particles containing the Gag protein produced by the packaging vector and the nucleic acid produced by the lentiviral vector. Preferably, this is achieved by cotransfection of the cells with the packaging vector and the lentiviral vector. The cells can also be transfected with a nucleic acid encoding an Env protein, preferably a VSV Glycoprotein G. Preferably, the lentiviral vector particles are capable of entry, reverse transcription, and expression in an appropriate host cell.

In one embodiment, the packaging vector or the lentiviral vector is stably integrated into cells, and the non-integrated vector is transfected into the cells to allow the formation of lentiviral vector particles.

In one embodiment, the method further comprises collecting the lentiviral vector produced by the cells.

In one embodiment, the method further comprises selecting for a packaging vector that packages a higher titer of the lentiviral vector than a same packaging vector encoding a subtype B Gag or Pol protein. Preferably, the titer is increased at least 1.5 or 2-fold relative to the packaging vector encoding a subtype B Gag or Pol protein.

Lentiviral Vector Particles

The invention also encompasses lentiviral vector particles comprising HIV-1 non-subtype B Gag and/or Pol proteins. The non-subtype B Gag and Pol proteins can comprise any of the features discussed herein.

The lentiviral vector particle comprises a nucleic acid comprising cis-acting sequences for packaging and reverse transcription, including a ψ site and primer binding site in association with Gag, Pol and Env proteins. Preferably, the nucleic acid comprises two HIV-1 LTR sequences. In one embodiment, one of the LTRs is deleted for U3 and R sequences. Preferably, the nucleic acid of the lentiviral vector particle comprises a central polypurine tract (cPPT) and a central terminal sequence (CTS). The nucleic acid preferably encodes a lentiviral or non-lentiviral protein, such as a selectable marker or tumor antigen. Preferably, the lentiviral vector particle comprises a VSV Glycoprotein.

Preferably, the lentiviral vector comprises an NIS-containing promoter. In one embodiment, the promoter is a β2m promoter.

In one embodiment, the lentiviral vector comprises one or more HIV antigen, preferably an HIV-1 antigen. Most preferably, the antigen is a Gag, Pol, Env, Vif, Vpr, Vpu, Nef, Tat, or Rev antigen.

The lentiviral vectors of the invention can be administered to a host cell, including a human host.

The lentiviral vector particle can contain a targeting mechanism for specific cell types. See, e.g., Yang et al., Targeting lentiviral vectors to specific cell types in vivo, PNAS 113(31):11479-11484 (2006), which is hereby incorporated by reference. Targeting can be achieved through an antibody that binds to a cell surface protein on a cell. The targeted cell type is preferably a dendritic cell, a T cell, a B cell. Targeting to dendritic cell type is preferred and can be accomplished through envelope proteins that specifically bind to a DC surface protein. See, e.g., Yang et al., Engineered Lentivector Targeting of Dendritic Cells for In Vivo, Nat Biotechnol. 2008 March; 26(3): 326-334, which is hereby incorporated by reference.

The present invention further relates to the use of the lentiviral vectors according to the invention, especially in the form of lentiviral vector particles, for the preparation of therapeutic compositions or vaccines which are capable of inducing or contributing to the occurrence or improvement of an immunogical reaction against epitopes, more particularly those encoded by the transgene present in the vectors.

EXAMPLES

Example 1. Plasmid Construction

The gag-pol gene was amplified by PCR, using two primers and pNDK-N, a clone of HIV-1 NDK, as template. In order to obtain pThV-GP-N plasmid, the PCR product was digested with Eagl/SalI and inserted in packaging construct p8.74, also digested by Eagl/SalI.

Example 2. Production of Lentiviral Vector by Transfection

Lentiviral vector stock was produced using pFLAP CMV GFP bis and pTHV-VSV.G (INDI-CO)bis in combination with p8.74 or pThV-GP-N. 36 transfections were done, 18 with p8.74 and 18 with pThV-GP-N. All the supernatant were stored at −80° C.

The plasmid pFLAP-CMV GFP bis encoded for the Green Fluorescence protein (GFP), which expression can be detected by flow cytometry.

Example 3. Titration of Lentiviral Vector Production

Vector titer was determined by the frequency of GFP expression in 293T cells. Cells were cultivated in 24-well plates, in DMEM containing 10% FBS, until they reached a density of $1 \times 10^5$ cells per well. The cells were then transduced with different volume of vector supernatant in a final volume of 300 μL. After 2 hours, 700 μl of fresh medium containing 10% FBS was added in each well. 72 hours after transduction, the medium was then removed and the cells washed in Dulbecco's phosphate-buffered saline (DPBS; Gibco). Cells were removed with 0.05% Trypsin-EDTA (Gibco). Trypsinization was stopped by the addition of 300 μl complete DMEM, and the cells were transferred to a tube for FACS, after which the number of GFP-expressing cells was counted with a FACSCalibur (BD Biosciences) using an excitation wavelength of 509 nm. Only the percent of GFP positive cells under 30% was considered.

The results are shown in FIG. 3. A significant difference between the pThV-GP-N and the p8.74 vectors productions was seen, with higher titers obtained using the pThV-GP-N plasmid. Indeed, the vector titer obtained with the packaging plasmid pThV-GP-N was 2 fold higher than the vector titer obtained with the classically used plasmid p8.74 ($p<0.001$ according to Student test).

Example 4. Increased Titer of Lentiviral Vector with pThV-GP-N

HIV-1 BRU and HIV-1 NDK viruses were made on 293T cells and used to transduced P4 CCR5 cells. These cells encompass a stable luciferase gene under the control of the HIV LTR: If they are transduced with TAT protein (which is the case when they are infected with a WT HIV), the LacZ gene is expressed and a luciferase expression can be measured. HIV-1 Gag p24 and luciferase expression were measured. The results are shown in FIG. 4, and confirm that wild type NDK virus has a higher transduction rate than the wild type BRU one.

Example 5. Increased p24 and Titer with pThV-GP-N

Different ratios of p8,74 and pSD GP NDK packaging vectors were used to produce lentiviral vector particles. For each ratio, the titer and the P24 level were measured. The results are shown in FIG. 5 and demonstrate that it is the presence of the NDK packaging plasmid that is responsible for the enhancement of the production titers and of the P24 level.

Example 6. Decreased p24 Processing with pThV-GP-N

Figure 6:
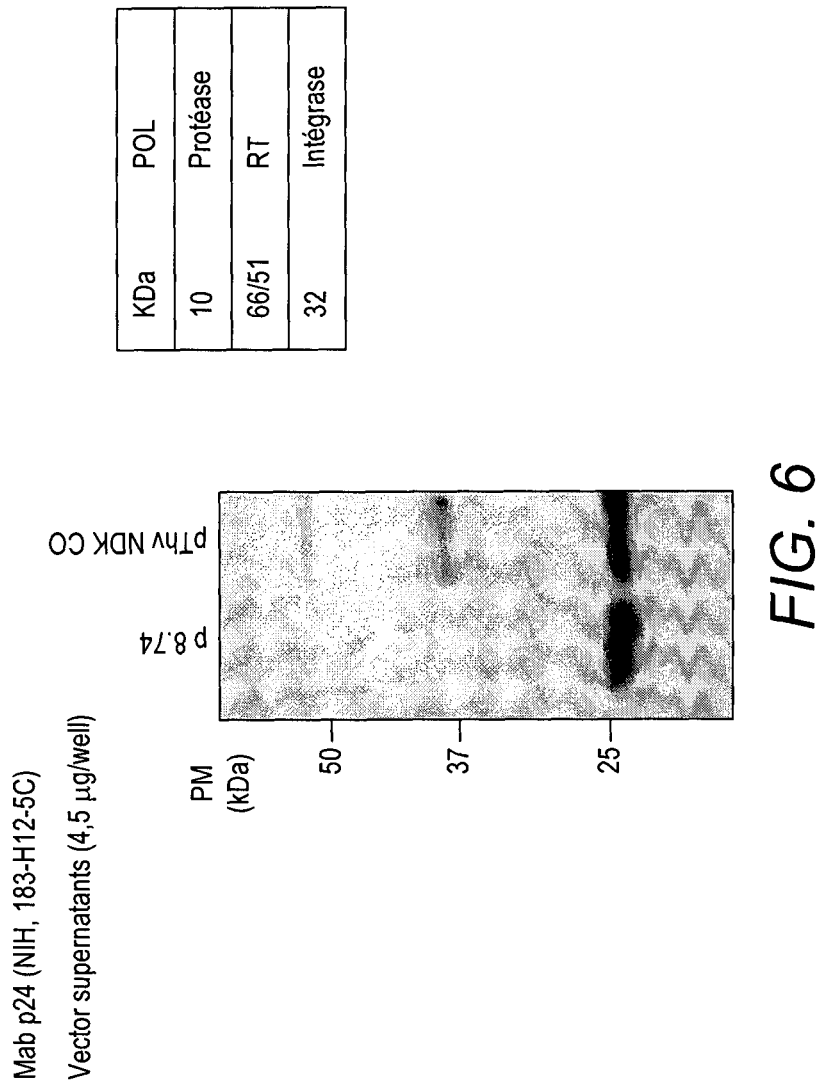

Packaging vectors p8.74 and pTHV-GP-N were used to produce supernatants containing lentiviral vector particles. Western blots were performed on the supernatants using the NIH anti-P24 MAB (183-H12-5C). The results are shown in FIG. 6, and confirm that the difference between the NDK and BRU packaging plasmids relies on the production of P24 protein and precursor, as the NDK seems to generate a higher P24 synthesis (presence of P24 precursor in the viral supernatant) when the BRU shows only P24 in viral supernatant.

We claim:

1. A lentiviral packaging vector to generate a replication defective lentiviral vector particle, the vector lacking a site and encoding the Gag-Pol protein of HIV-1 NDK, wherein the Gag-Pol protein comprises the amino acid sequence of SEQ ID NO:2 wherein the coding sequence of the Gag-Pol protein is operably linked to an expression control sequence.

2. The vector of claim 1, wherein the vector is a plasmid comprising a Cytomegalovirus promoter.

3. A cell comprising the vector of claim 1.

4. The cell of claim 3, wherein the vector is an integrative vector.

5. A method for generating the packaging vector of claim 1, the method comprising inserting the nucleotide sequence encoding the Gag-Pol protein of HIV-1 NDK into a plasmid under the control of a non-HIV promoter to generate the packaging vector.

6. A method for generating a lentiviral vector particle, the method comprising administering the packaging vector of claim 1 to a cell with a lentiviral vector comprising 5' and 3' lentiviral long terminal repeats and a sequence encoding lentiviral envelope.

7. The method of claim 6, wherein the packaging vector and the lentiviral vector are plasmids.

8. The method of claim 6, wherein the packaging vector is a non-integrative vector.

9. The method of claim 6, wherein the packaging vector is an integrative vector.

10. A lentiviral vector particle comprising Gag-Pol protein of HIV-1 NDK and VSV Env glycoproteins, wherein the Gag-Pol protein comprises the amino acid sequence of SEQ ID NO:2.

11. The lentiviral vector particle of claim 10, wherein the lentiviral particle encodes a tumor antigen.

12. The lentiviral vector particle of claim 10, wherein the lentiviral particle comprises an LTR deleted for U3 and R regions.

13. The lentiviral vector particle of claim 10, wherein the lentiviral particle does not comprise HIV-1 Env proteins.

* * * * *

SEQUENCE LISTING

<160> NUMBER OF SEQ ID NOS: 67

<210> SEQ ID NO 1
<211> LENGTH: 4298
<212> TYPE: DNA
<213> ORGANISM: Human immunodeficiency virus type 1

<400> SEQUENCE: 1

| | | | | | |
|---|---|---|---|---|---|
| atgggtgcga | gagcgtcagt | attaagcggg | ggaaaattag | atacatggga | aagaattcgg | 60 |
| ttacggccag | gaggaaagaa | aaaatatgca | ctaaaacatt | tgatatgggc | aagcagggag | 120 |
| ctagaacgat | ttacacttaa | tcctggcctt | ttagagacat | cagaaggctg | taaacaaata | 180 |
| ataggacagc | tacaaccatc | tattcaaaca | ggatcagaag | aaattagatc | attatataat | 240 |
| acagtagcaa | ccctctattg | tgtacatgaa | aggatagagg | taaaagacac | caaagaagct | 300 |
| gtagaaaaga | tggaggaaga | acaaaacaaa | agtaagaaaa | agacacagca | agcagcagct | 360 |
| gatagcagcc | aggtcagcca | aaattaccct | atagtgcaga | acctacaggg | gcaaatggta | 420 |
| catcaggcca | tatcacctag | aactttgaac | gcatgggtaa | aagtaataga | agaaaaggcc | 480 |
| ttcagcccgg | aagtaatacc | catgttttca | gcattatcag | aaggagccac | cccacaagat | 540 |
| ttaaacacca | tgctaaacac | agtgggggga | catcaagcag | ctatgcaaat | gctaaaagag | 600 |
| accatcaatg | acgaagctgc | agaatgggac | agattacatc | cagtgcatgc | agggcctgtt | 660 |
| gcaccaggcc | aaatgagaga | accaagggga | agtgatatag | caggaactac | tagtacccct | 720 |
| caggaacaaa | tagcatggat | gacaagcaac | ccacctatcc | cagtaggaga | aatctataaa | 780 |
| agatggataa | tcctgggatt | aaataaaata | gtaagaatgt | atagccctgt | cagcattttg | 840 |
| gacataagac | agggaccaaa | ggaacctttt | agagactatg | tagaccggtt | ctataaaact | 900 |
| ctaagagccg | agcaagcttc | acaggatgta | aaaaactgga | tgacagaaac | cttgttggtc | 960 |
| caaaatgcaa | acccagattg | taaaactatc | ttaaaagcat | tgggaccaca | ggctacacta | 1020 |
| gaagaaatga | tgacagcatg | ccagggagtg | ggggggcccg | gccataaagc | aagagttttg | 1080 |
| gctgaggcaa | tgagccaagt | aacaggttca | gctactgcag | taatgatgca | gagaggcaat | 1140 |
| tttaagggcc | caagaaaaag | tattaagtgt | ttcaactgtg | gcaaggaagg | gcacacagca | 1200 |
| aaaaattgca | gggcccctag | aaaaaagggc | tgttggaaat | gcgaaggga | aggacaccaa | 1260 |
| atgaaagatt | gcactgaaag | acaggctaat | tttttaggga | agatttggcc | ttcccacaag | 1320 |
| ggaaggccgg | ggaattttct | tcagagcaga | ccagagccaa | cagccccacc | agcagagagc | 1380 |
| ttcgggtttg | gggaggagat | aacccccctct | cagaaacagg | agcagaaaga | caaggaactg | 1440 |
| tatcctttag | cttccctcaa | atcactcttt | ggcaacgacc | cctcgtcaca | ataaagatag | 1500 |
| ggggacagct | aaaggaagct | ctattagata | caggagcaga | tgatacagta | ttagaagaaa | 1560 |

```
taaatttgcc aggaaaatgg aagccaaaaa tgatagggg  aattggaggt tttatcaaag    1620
taagacagta tgatcaaata ctcatagaaa tctgtggata taaagctatg ggtacagtat    1680
tagtaggacc tacacctgtc aacataattg gaagaaattt gttgacccag attggctgca    1740 cttttaaattt tccaattagt cctattgaaa ctgtaccagt aaaattaaag ccaggaatgg    1800
atggcccaaa agttaaacaa tggccattga cgaagaaaaa ataaaagcat taacagaaat    1860
ttgtacagaa atggaaaagg aaggaaaaat ttcaagaatt gggcctgaaa atccatataa    1920
tactccaata tttgccataa agaaaaaaga cagtaccaag tggagaaaat tagtagattt    1980
cagagaactt aataagagaa ctcaagattt ctgggaggtt caattaggaa taccgcatcc    2040
tgcagggctg aaaaagaaaa aatcagtaac agtactggat gtgggtgatg catatttctc    2100
agttccctta tgatgaagatt ttaggaaata taccgcattt accataccta gtataaacaa    2160
tgagacacca gggattagat atcagtacaa tgtgctccca cagggatgga aaggatcacc    2220
ggcaatattc caaagtagca tgacaaaaat cttagagccc tttagaaaac aaaatccaga    2280
aatagttatc tatcaataca tggatgattt gtatgtagga tctgacttag aaatagggca    2340
gcatagaaca aaaatagagg aattaagaga acatctattg aggtggggat ttaccacacc    2400
agataaaaaa catcagaaag aacctccatt tctttggatg ggttatgaac tccatcctga    2460
taaatggaca gtacagccta taaacctgcc agaaaaagaa agctggactg tcaatgatat    2520
acagaagtta gtggggaaat taaactgggc aagccagatt tatgcaggaa ttaaagtaaa    2580
gcaattatgt aaactcctta ggggaaccaa agcactaaca gaagtagtac cactaacaga    2640
agaagcagaa ttagaactgg cagaaaacag ggaaattcta aaagaaccag tacatggagt    2700
gtattatgac ccatcaaaag acttaatagc agaactacag aaacaagggg acggccaatg    2760
gacataccaa atttatcaag aaccatttaa aaatctaaaa acaggaaagt atgcaagaac    2820
gaggggtgcc cacactaatg atgtaaaaca attaacagag gcagtgcaaa aaatagccac    2880
agaaagcata gtgatatggg gaaagactcc taaatttaaa ctacccatac aaaaggaaac    2940
atgggaaaca tggtggatag agtattggca agccacctgg attcctgagt gggaatttgt    3000
caatacccct ccttttagtaa aattatggta ccagttagag aaggaaccca ataggagc    3060 agaaactttc tatgtagatg gggcagctaa tagagagact aaattaggaa aagcaggata    3120
tgttactgac agaggaagac agaaagttgt ccctttcact gacacgacaa atcagaagac    3180
tgagttacaa gcaattaatc tagctttaca ggattcggga ttagaagtaa acatagtaac    3240
agattcacaa tatgcactag gaatcattca agcacaacca gataagagtg aatcagagtt    3300
agtcagtcaa ataatagagc agctaataaa aaggaaaag gtttacctgg catgggtacc    3360
agcacacaaa ggaattggag gaaatgaaca agtagataaa ttagtcagtc agggaatcag    3420
gaaagtacta ttttttggatg aatagataa ggctcaggaa gaacatgaga aatatcacaa    3480 caattgggaga gcaatggcta gtgattttaa cctaccacct gtggtagcga aagaaatagt    3540
agctagctgt gataaatgtc agctaaaagg agaagccatg catggacaag tagactgtag    3600
tccaggaata tggcaattag attgtacaca tctggaagga aaagttatcc tggtagcagt    3660
tcatgtagcc agtggctata tagaagcaga agttattcca gcagaaacgg ggcaagaaac    3720
agcatacttt ctcttaaaat tagcaggaag atggccagta aaagtagtac atacagataa    3780
tggcagcaat ttcaccagtg ctacagttaa ggccgcctgt tggtgggcag ggatcaaaca    3840
ggaatttgga attccctaca atccccaaag tcaaggagta gtagaatcta tgaataaaga    3900
```

-continued

```
attaaagaaa attataggac aggtaagaga tcaagctgaa catcttaaga cagcagtaca    3960
aatggcagta tttatccaca attttaaaag aaaaggggggg attgggggat acagtgcagg   4020
ggaaagaata atagacataa tagcaacaga catacaaact agagaattac aaaaacaaat    4080
cataaaaatt caaaatttc gggtttatta cagggacagc agagatccaa tttggaaagg     4140
accagcaaag cttctctgga aaggtgaagg ggcagtagta atacaagaca atagtgacat    4200
aaaggtagta ccaagaagaa aagtaaagat cattagggat tatggaaaac agatggcagg    4260
tgatgattgt gtggcaagta gacaggatga ggattaac                            4298
```

<210> SEQ ID NO 2
<211> LENGTH: 1499
<212> TYPE: PRT
<213> ORGANISM: Human immunodeficiency virus type 1

<400> SEQUENCE: 2

```
Met Gly Ala Arg Ala Ser Val Leu Ser Gly Gly Lys Leu Asp Ala Trp
1               5                  10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Ile Ala Leu Asn Pro
        35                  40                  45

Gly Leu Leu Glu Thr Ser Glu Gly Cys Lys Gln Ile Ile Gly Gln Leu
    50                  55                  60

Gln Pro Ser Ile Gln Thr Gly Ser Glu Glu Leu Arg Ser Leu Tyr Asn
65                  70                  75                  80

Thr Ile Ala Thr Leu Tyr Cys Val His Glu Arg Ile Glu Val Lys Asp
                85                  90                  95

Thr Lys Glu Ala Val Glu Lys Met Glu Glu Glu Gln Asn Lys Ser Lys
            100                 105                 110

Lys Lys Thr Gln Gln Ala Ala Ala Asp Ser Ser Gln Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Ser Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Glu Thr Ile Asn Asp Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Ile Pro Val Gly
                245                 250                 255

Glu Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Tyr Lys Thr Leu Arg Ala Glu
    290                 295                 300
```

```
Gln Ala Ser Gln Asp Val Lys Asn Trp Met Thr Glu Thr Leu Leu Val
305                 310                 315                 320

Gln Asn Ala Asn Pro Asp Cys Lys Thr Ile Leu Lys Ala Leu Gly Pro
            325                 330                 335

Gln Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Val Thr
        355                 360                 365

Gly Ser Val Thr Ala Val Met Met Gln Arg Gly Asn Phe Lys Gly Pro
    370                 375                 380

Arg Lys Ser Ile Lys Cys Phe Asn Cys Gly Lys Glu Gly His Thr Ala
385                 390                 395                 400

Lys Asn Cys Arg Ala Pro Arg Lys Lys Gly Cys Trp Lys Cys Gly Arg
            405                 410                 415

Glu Gly His Gln Met Lys Asp Cys Ser Glu Arg Gln Ala Asn Phe Leu
        420                 425                 430

Gly Lys Ile Trp Pro Ser His Lys Gly Arg Pro Gly Asn Phe Leu Gln
    435                 440                 445

Ser Arg Pro Glu Pro Thr Ala Pro Pro Ala Glu Ser Phe Gly Phe Gly
450                 455                 460

Glu Glu Ile Thr Pro Ser Gln Lys Gln Glu Gln Lys Asp Lys Glu Leu
465                 470                 475                 480

Tyr Pro Leu Ala Ser Leu Lys Ser Leu Phe Gly Asn Asp Pro Ser Ser
            485                 490                 495

Gln Phe Phe Arg Glu Asp Leu Ala Phe Pro Gln Gly Lys Ala Gly Glu
        500                 505                 510

Phe Ser Ser Glu Gln Thr Arg Ala Asn Ser Pro Thr Ser Arg Glu Leu
    515                 520                 525

Arg Val Trp Gly Gly Asp Asn Pro Leu Ser Glu Thr Gly Ala Glu Gly
530                 535                 540

Gln Gly Thr Val Ser Phe Ser Phe Pro Gln Ile Thr Leu Trp Gln Arg
545                 550                 555                 560

Pro Leu Val Thr Ile Lys Ile Gly Gly Gln Leu Lys Glu Ala Leu Leu
            565                 570                 575

Asp Thr Gly Ala Asp Asp Thr Val Leu Glu Glu Met Asn Leu Pro Gly
        580                 585                 590

Lys Trp Lys Pro Lys Met Ile Gly Gly Ile Gly Gly Phe Ile Lys Val
    595                 600                 605

Arg Gln Tyr Asp Gln Ile Leu Ile Glu Ile Cys Gly Tyr Lys Ala Met
610                 615                 620

Gly Thr Val Leu Val Gly Pro Thr Pro Val Asn Ile Ile Gly Arg Asn
625                 630                 635                 640

Leu Leu Thr Gln Ile Gly Cys Thr Leu Asn Phe Pro Ile Ser Pro Ile
            645                 650                 655

Glu Thr Val Pro Val Lys Leu Lys Pro Gly Met Asp Gly Pro Lys Val
        660                 665                 670

Lys Gln Trp Pro Leu Thr Glu Glu Lys Ile Lys Ala Leu Thr Glu Ile
    675                 680                 685

Cys Thr Glu Met Glu Lys Glu Gly Lys Ile Ser Arg Ile Gly Pro Glu
690                 695                 700

Asn Pro Tyr Asn Thr Pro Ile Phe Ala Ile Lys Lys Lys Asp Ser Thr
705                 710                 715                 720

Lys Trp Arg Lys Leu Val Asp Phe Arg Glu Leu Asn Lys Arg Thr Gln
```

-continued

```
                725                 730                 735
Asp Phe Trp Glu Val Gln Leu Gly Ile Pro His Pro Ala Gly Leu Lys
            740                 745                 750
Lys Lys Lys Ser Val Thr Val Leu Asp Val Gly Asp Ala Tyr Phe Ser
            755                 760                 765
Val Pro Leu Asp Glu Asp Phe Arg Lys Tyr Thr Ala Phe Thr Ile Pro
770                 775                 780
Ser Ile Asn Asn Glu Thr Pro Gly Ile Arg Tyr Gln Tyr Asn Val Leu
785                 790                 795                 800
Pro Gln Gly Trp Lys Gly Ser Pro Ala Ile Phe Gln Ser Ser Met Thr
                805                 810                 815
Lys Ile Leu Glu Pro Phe Arg Lys Gln Asn Pro Glu Ile Val Ile Tyr
            820                 825                 830
Gln Tyr Met Asp Asp Leu Tyr Val Gly Ser Asp Leu Glu Ile Gly Gln
            835                 840                 845
His Arg Thr Lys Ile Glu Glu Leu Arg Glu His Leu Leu Arg Trp Gly
            850                 855                 860
Phe Thr Thr Pro Asp Lys Lys His Gln Lys Glu Pro Pro Phe Leu Trp
865                 870                 875                 880
Met Gly Tyr Glu Leu His Pro Asp Lys Trp Thr Val Gln Pro Ile Lys
                885                 890                 895
Leu Pro Glu Lys Glu Ser Trp Thr Val Asn Asp Ile Gln Lys Leu Val
                900                 905                 910
Gly Lys Leu Asn Trp Ala Ser Gln Ile Tyr Ala Gly Ile Lys Val Lys
            915                 920                 925
Gln Leu Cys Lys Leu Leu Arg Gly Thr Lys Ala Leu Thr Glu Val Val
            930                 935                 940
Pro Leu Thr Glu Glu Ala Glu Leu Glu Leu Ala Glu Asn Arg Glu Ile
945                 950                 955                 960
Leu Lys Glu Pro Val His Gly Val Tyr Tyr Asp Pro Ser Lys Asp Leu
                965                 970                 975
Ile Ala Glu Leu Gln Lys Gln Gly Asp Gly Gln Trp Thr Tyr Gln Ile
                980                 985                 990
Tyr Gln Glu Pro Phe Lys Asn Leu  Lys Thr Gly Lys Tyr  Ala Arg Thr
            995                 1000                1005
Arg Gly  Ala His Thr Asn Asp  Val Lys Gln Leu Thr  Glu Ala Val
            1010                1015                1020
Gln Lys  Ile Ala Thr Glu Ser  Ile Val Ile Trp Gly  Lys Thr Pro
            1025                1030                1035
Lys Phe  Lys Leu Pro Ile Gln  Lys Glu Thr Trp Glu  Thr Trp Trp
            1040                1045                1050
Ile Glu  Tyr Trp Gln Ala Thr  Trp Ile Pro Glu Trp  Glu Phe Val
            1055                1060                1065
Asn Thr  Pro Pro Leu Val Lys  Leu Trp Tyr Gln Leu  Glu Lys Glu
            1070                1075                1080
Pro Ile  Ile Gly Ala Glu Thr  Phe Tyr Val Asp Gly  Ala Ala Asn
            1085                1090                1095
Arg Glu  Thr Lys Leu Gly Lys  Ala Gly Tyr Val Thr  Asp Arg Gly
            1100                1105                1110
Arg Gln  Lys Val Val Pro Phe  Thr Asp Thr Thr Asn  Gln Lys Thr
            1115                1120                1125
Glu Leu  Gln Ala Ile Asn Leu  Ala Leu Gln Asp Ser  Gly Leu Glu
            1130                1135                1140
```

```
Val Asn Ile Val Thr Asp Ser Gln Tyr Ala Leu Gly Ile Ile Gln
    1145                1150                1155

Ala Gln Pro Asp Lys Ser Glu Ser Glu Leu Val Ser Gln Ile Ile
    1160                1165                1170

Glu Gln Leu Ile Lys Lys Glu Lys Val Tyr Leu Ala Trp Val Pro
    1175                1180                1185

Ala His Lys Gly Ile Gly Gly Asn Glu Gln Val Asp Lys Leu Val
    1190                1195                1200

Ser Gln Gly Ile Arg Lys Val Leu Phe Leu Asp Gly Ile Asp Lys
    1205                1210                1215

Ala Gln Glu Glu His Glu Lys Tyr His Asn Asn Trp Arg Ala Met
    1220                1225                1230

Ala Ser Asp Phe Asn Leu Pro Pro Val Val Ala Lys Glu Ile Val
    1235                1240                1245

Ala Ser Cys Asp Lys Cys Gln Leu Lys Gly Glu Ala Met His Gly
    1250                1255                1260

Gln Val Asp Cys Ser Pro Gly Ile Trp Gln Leu Asp Cys Thr His
    1265                1270                1275

Leu Glu Gly Lys Val Ile Leu Val Ala Val His Val Ala Ser Gly
    1280                1285                1290

Tyr Ile Glu Ala Glu Val Ile Pro Ala Glu Thr Gly Gln Glu Thr
    1295                1300                1305

Ala Tyr Phe Leu Leu Lys Leu Ala Gly Arg Trp Pro Val Lys Val
    1310                1315                1320

Val His Thr Asp Asn Gly Ser Asn Phe Thr Ser Ala Thr Val Lys
    1325                1330                1335

Ala Ala Cys Trp Trp Ala Gly Ile Lys Gln Glu Phe Gly Ile Pro
    1340                1345                1350

Tyr Asn Pro Gln Ser Gln Gly Val Val Glu Ser Met Asn Lys Glu
    1355                1360                1365

Leu Lys Lys Ile Ile Gly Gln Val Arg Asp Gln Ala Glu His Leu
    1370                1375                1380

Lys Thr Ala Val Gln Met Ala Val Phe Ile His Asn Phe Lys Arg
    1385                1390                1395

Lys Gly Gly Ile Gly Gly Tyr Ser Ala Gly Glu Arg Ile Ile Asp
    1400                1405                1410

Ile Ile Ala Thr Asp Ile Gln Thr Arg Glu Leu Gln Lys Gln Ile
    1415                1420                1425

Ile Lys Ile Gln Asn Phe Arg Val Tyr Tyr Arg Asp Ser Arg Asp
    1430                1435                1440

Pro Ile Trp Lys Gly Pro Ala Lys Leu Leu Trp Lys Gly Glu Gly
    1445                1450                1455

Ala Val Val Ile Gln Asp Asn Ser Asp Ile Lys Val Val Pro Arg
    1460                1465                1470

Arg Lys Val Lys Ile Ile Arg Asp Tyr Gly Lys Gln Met Ala Gly
    1475                1480                1485

Asp Asp Cys Val Ala Ser Arg Gln Asp Glu Asp
    1490                1495
```

<210> SEQ ID NO 3
<211> LENGTH: 129
<212> TYPE: PRT
<213> ORGANISM: Human immunodeficiency virus type 1

<400> SEQUENCE: 3

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
        35                  40                  45

Gly Leu Leu Glu Thr Ser Glu Gly Cys Lys Gln Ile Ile Gly Gln Leu
    50                  55                  60

Gln Pro Ser Ile Gln Thr Gly Ser Glu Glu Ile Arg Ser Leu Tyr Asn
65              70                  75                  80

Thr Val Ala Thr Leu Tyr Cys Val His Glu Arg Ile Glu Val Lys Asp
                85                  90                  95

Thr Lys Glu Ala Val Glu Lys Met Glu Glu Gln Asn Lys Ser Lys
                100                 105                 110

Lys Lys Thr Gln Gln Ala Ala Ala Asp Ser Ser Gln Val Ser Gln Asn
            115                 120                 125

Tyr

<210> SEQ ID NO 4
<211> LENGTH: 129
<212> TYPE: PRT
<213> ORGANISM: Human immunodeficiency virus type 1

<400> SEQUENCE: 4

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
        35                  40                  45

Gly Leu Leu Glu Thr Ser Glu Gly Cys Lys Gln Ile Ile Gly Gln Leu
    50                  55                  60

Gln Pro Ser Ile Gln Thr Gly Ser Glu Glu Ile Arg Ser Leu Tyr Asn
65              70                  75                  80

Thr Val Ala Thr Leu Tyr Cys Val His Glu Arg Ile Glu Val Lys Asp
                85                  90                  95

Thr Lys Glu Ala Val Glu Lys Met Glu Glu Gln Asn Lys Ser Lys
                100                 105                 110

Lys Lys Thr Gln Gln Ala Ala Ala Asp Ser Ser Gln Val Ser Gln Asn
            115                 120                 125

Tyr

<210> SEQ ID NO 5
<211> LENGTH: 132
<212> TYPE: PRT
<213> ORGANISM: Human immunodeficiency virus type 1

<400> SEQUENCE: 5

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

```
Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly His Ser Asn Gln Val
            115                 120                 125

Ser Gln Asn Tyr
    130
```

<210> SEQ ID NO 6
<211> LENGTH: 75
<212> TYPE: PRT
<213> ORGANISM: Human immunodeficiency virus type 1

<400> SEQUENCE: 6

```
Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
                 20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu
 65                  70                  75
```

<210> SEQ ID NO 7
<211> LENGTH: 73
<212> TYPE: PRT
<213> ORGANISM: Human immunodeficiency virus type 1

<400> SEQUENCE: 7

```
Ala Arg Ala Ser Val Leu Ser Gly Gly Glu Leu Asp Arg Trp Glu Lys
  1               5                  10                  15

Ile Arg Leu Arg Pro Gly Gly Lys Lys Lys Tyr Arg Leu Lys His Ile
                 20                  25                  30

Val Trp Ala Ser Arg Glu Leu Glu Arg Phe Ala Val Asn Pro Gly Leu
             35                  40                  45

Leu Glu Thr Thr Glu Gly Cys Arg Gln Ile Leu Gly Gln Leu Gln Pro
    50                  55                  60

Ser Leu Gln Thr Gly Ser Glu Glu Leu
 65                  70
```

<210> SEQ ID NO 8
<211> LENGTH: 75
<212> TYPE: PRT
<213> ORGANISM: Human immunodeficiency virus type 1

<400> SEQUENCE: 8

```
Met Gly Ala Arg Ala Ser Val Leu Ser Gly Gly Gln Leu Asp Arg Trp
  1               5                  10                  15

Glu Lys Ile Arg Leu Arg Pro Gly Gly Lys Lys Lys Tyr Arg Leu Lys
                 20                  25                  30

His Leu Val Trp Ala Ser Arg Glu Leu Glu Arg Phe Ala Val Asn Pro
```

```
                35                  40                  45
Gly Leu Leu Glu Thr Ser Glu Gly Cys Arg Gln Ile Leu Glu Gln Leu
    50                  55                  60

Gln Pro Ser Leu Gln Thr Gly Ser Glu Glu Leu
65                  70                  75

<210> SEQ ID NO 9
<211> LENGTH: 75
<212> TYPE: PRT
<213> ORGANISM: Human immunodeficiency virus type 1

<400> SEQUENCE: 9

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
                35                  40                  45

Gly Leu Leu Glu Thr Ser Gly Gly Cys Arg Gln Ile Leu Glu Gln Leu
    50                  55                  60

Gln Pro Ser Leu Gln Thr Gly Ser Glu Glu Leu
65                  70                  75

<210> SEQ ID NO 10
<211> LENGTH: 75
<212> TYPE: PRT
<213> ORGANISM: Human immunodeficiency virus type 1

<400> SEQUENCE: 10

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
                20                  25                  30

His Ile Val Trp Ala Ser Arg Glu Leu Glu Arg Phe Ala Ile Asn Pro
                35                  40                  45

Gly Leu Leu Glu Thr Ser Ala Gly Cys Arg Gln Ile Leu Gly Gln Leu
    50                  55                  60

His Pro Ser Leu Gln Thr Gly Ser Glu Glu Leu
65                  70                  75

<210> SEQ ID NO 11
<211> LENGTH: 73
<212> TYPE: PRT
<213> ORGANISM: Human immunodeficiency virus type 1

<400> SEQUENCE: 11

Ala Arg Ala Ser Val Leu Ser Gly Gly Glu Leu Asp Lys Trp Glu Lys
1               5                   10                  15

Ile Arg Leu Arg Pro Gly Gly Lys Lys Lys Tyr Arg Leu Lys His Ile
                20                  25                  30

Val Trp Ala Ser Arg Glu Leu Glu Arg Phe Ala Val Asn Pro Gly Leu
                35                  40                  45

Leu Glu Thr Ser Glu Gly Cys Arg Gln Ile Leu Ala Gln Leu Gln Pro
    50                  55                  60

Ser Leu Pro Thr Gly Ser Glu Glu Leu
65                  70

<210> SEQ ID NO 12
```

```
<211> LENGTH: 75
<212> TYPE: PRT
<213> ORGANISM: Human immunodeficiency virus type 1

<400> SEQUENCE: 12

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu
65                  70                  75

<210> SEQ ID NO 13
<211> LENGTH: 73
<212> TYPE: PRT
<213> ORGANISM: Human immunodeficiency virus type 1

<400> SEQUENCE: 13

Ala Arg Ala Ser Ile Leu Ser Gly Gly Glu Leu Asp Arg Trp Glu Lys
1               5                   10                  15

Ile Arg Leu Arg Pro Gly Gly Lys Lys Lys Tyr Lys Leu Lys His Ile
            20                  25                  30

Val Trp Ala Ser Arg Glu Leu Glu Arg Phe Ala Val Asn Pro Gly Leu
        35                  40                  45

Leu Glu Thr Ser Glu Gly Cys Ile Gln Ile Leu Gly Gln Leu Gln Pro
    50                  55                  60

Ser Leu Gln Thr Gly Ser Glu Glu Leu
65                  70

<210> SEQ ID NO 14
<211> LENGTH: 75
<212> TYPE: PRT
<213> ORGANISM: Human immunodeficiency virus type 1

<400> SEQUENCE: 14

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Val Val Trp Ala Ser Arg Glu Leu Glu Arg Phe Ala Val Asn Pro
        35                  40                  45

Gly Leu Leu Glu Thr Ser Glu Gly Cys Arg Lys Ile Leu Gly Gln Leu
    50                  55                  60

Gln Pro Ser Leu Gln Thr Gly Ser Glu Glu Leu
65                  70                  75

<210> SEQ ID NO 15
<211> LENGTH: 75
<212> TYPE: PRT
<213> ORGANISM: Human immunodeficiency virus type 1

<400> SEQUENCE: 15

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Gln Tyr Lys Leu Lys
```

```
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Arg Gln Ile Leu Glu Gln Leu
    50                  55                  60

Gln Pro Ser Leu Gln Thr Gly Ser Glu Glu Ile
65                  70                  75

<210> SEQ ID NO 16
<211> LENGTH: 75
<212> TYPE: PRT
<213> ORGANISM: Human immunodeficiency virus type 1

<400> SEQUENCE: 16

Met Gly Ala Arg Ala Ser Ile Leu Ser Gly Gly Glu Leu Asp Arg Trp
1               5                   10                  15

Glu Lys Ile Arg Leu Arg Pro Gly Gly Lys Lys Gln Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Gly Gly Cys Lys Gln Ile Leu Ala Gln Leu
    50                  55                  60

His Pro Ser Leu Gln Thr Gly Ser Glu Glu Leu
65                  70                  75

<210> SEQ ID NO 17
<211> LENGTH: 73
<212> TYPE: PRT
<213> ORGANISM: Human immunodeficiency virus type 1

<400> SEQUENCE: 17

Ala Arg Ala Ser Ile Leu Ser Gly Gly Glu Leu Asp Arg Trp Glu Lys
1               5                   10                  15

Ile Arg Leu Arg Pro Gly Gly Lys Lys Arg Tyr Arg Leu Lys His Ile
            20                  25                  30

Val Trp Ala Ser Arg Glu Leu Glu Arg Phe Ala Val Asn Pro Gly Leu
        35                  40                  45

Leu Glu Thr Ser Glu Gly Cys Lys Gln Ile Ile Arg Gln Leu Gln Pro
    50                  55                  60

Ser Leu Gln Thr Gly Ser Glu Glu Leu
65                  70

<210> SEQ ID NO 18
<211> LENGTH: 75
<212> TYPE: PRT
<213> ORGANISM: Human immunodeficiency virus type 1

<400> SEQUENCE: 18

Met Gly Ala Arg Ala Ser Val Leu Ser Gly Gly Glu Leu Asp Arg Trp
1               5                   10                  15

Glu Arg Ile Arg Leu Arg Pro Arg Gly Lys Lys Lys Tyr Gln Leu Lys
            20                  25                  30

His Ile Val Trp Ala Ser Arg Glu Leu Glu Arg Phe Ser Val Asn Pro
        35                  40                  45

Gly Leu Leu Glu Thr Ser Glu Gly Cys Arg Gln Ile Leu Arg Gln Leu
    50                  55                  60

Gln Pro Ala Leu Gln Thr Gly Ser Glu Asp Phe
65                  70                  75
```

<210> SEQ ID NO 19
<211> LENGTH: 75
<212> TYPE: PRT
<213> ORGANISM: Human immunodeficiency virus type 1

<400> SEQUENCE: 19

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Leu Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu
65                  70                  75

<210> SEQ ID NO 20
<211> LENGTH: 75
<212> TYPE: PRT
<213> ORGANISM: Human immunodeficiency virus type 1

<400> SEQUENCE: 20

Met Gly Ala Arg Ala Ser Val Leu Ser Gly Gly Glu Leu Asp Arg Trp
1               5                   10                  15

Glu Arg Ile Arg Leu Arg Pro Gly Gly Ser Lys Lys Tyr Lys Leu Lys
            20                  25                  30

His Ile Val Trp Ala Ser Arg Glu Leu Glu Arg Phe Ala Val Asn Pro
        35                  40                  45

Ser Leu Leu Glu Thr Ser Glu Gly Cys Lys Gln Ile Leu Gly Gln Leu
    50                  55                  60

Gln Pro Ser Leu Gln Thr Gly Ser Glu Glu Leu
65                  70                  75

<210> SEQ ID NO 21
<211> LENGTH: 75
<212> TYPE: PRT
<213> ORGANISM: Human immunodeficiency virus type 1

<400> SEQUENCE: 21

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Gln Leu Lys
            20                  25                  30

His Ile Val Trp Ala Ser Arg Glu Leu Glu Arg Phe Ala Val Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu
65                  70                  75

<210> SEQ ID NO 22
<211> LENGTH: 75
<212> TYPE: PRT
<213> ORGANISM: Human immunodeficiency virus type 1

<400> SEQUENCE: 22

Met Gly Ala Arg Ala Ser Val Leu Ser Gly Gly Glu Leu Asp Lys Trp

```
                1               5                  10                 15
Glu Arg Ile Arg Leu Arg Pro Gly Gly Lys Lys Tyr Lys Leu Lys
                20                 25                 30

His Ile Val Trp Ala Ser Arg Glu Leu Glu Arg Phe Ala Val Asn Pro
            35                 40                 45

Gly Leu Leu Glu Thr Ser Glu Gly Cys Arg Gln Ile Ile Gly Gln Leu
    50                 55                 60

Gln Pro Ser Leu Gln Thr Gly Ser Glu Glu Leu
65                  70                  75

<210> SEQ ID NO 23
<211> LENGTH: 75
<212> TYPE: PRT
<213> ORGANISM: Human immunodeficiency virus type 1

<400> SEQUENCE: 23

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
                20                 25                 30

His Val Val Trp Ala Ser Arg Glu Leu Glu Arg Phe Ala Val Asn Pro
            35                 40                 45

Gly Leu Leu Glu Thr Ala Glu Gly Cys Lys Gln Ile Leu Ala Gln Leu
    50                 55                 60

His Pro Ser Leu Gln Thr Gly Ser Glu Glu Leu
65                  70                  75

<210> SEQ ID NO 24
<211> LENGTH: 72
<212> TYPE: PRT
<213> ORGANISM: Human immunodeficiency virus type 1
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid

<400> SEQUENCE: 24

Arg Ala Ser Val Leu Ser Gly Gly Glu Leu Asp Arg Trp Glu Lys Ile
1               5                   10                  15

Arg Xaa Arg Gln Gly Gly Lys Lys Tyr Lys Leu Lys His Ile Val
            20                 25                 30

Trp Ala Ser Arg Glu Leu Glu Arg Phe Ala Val Asn Pro Gly Leu Leu
        35                 40                 45

Glu Thr Xaa Glu Gly Cys Arg Gln Ile Leu Glu Gln Leu Gln Pro Ala
    50                 55                 60

Leu Gln Thr Gly Ser Glu Glu Leu
65                  70

<210> SEQ ID NO 25
<211> LENGTH: 75
<212> TYPE: PRT
<213> ORGANISM: Human immunodeficiency virus type 1

<400> SEQUENCE: 25

Met Gly Ala Arg Ala Ser Val Leu Ser Gly Gly Glu Leu Asp Arg Trp
1               5                   10                  15
```

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Gly Gly Cys Arg Gln Ile Leu Gly Gln Leu
    50                  55                  60

Gln Pro Ser Leu Gln Thr Gly Ser Glu Glu Leu
65                  70                  75

<210> SEQ ID NO 26
<211> LENGTH: 75
<212> TYPE: PRT
<213> ORGANISM: Human immunodeficiency virus type 1

<400> SEQUENCE: 26

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
        35                  40                  45

Gly Leu Leu Glu Thr Ser Glu Gly Cys Lys Gln Ile Ile Gly Gln Leu
    50                  55                  60

Gln Pro Ser Ile Gln Thr Gly Ser Glu Glu Ile
65                  70                  75

<210> SEQ ID NO 27
<211> LENGTH: 75
<212> TYPE: PRT
<213> ORGANISM: Human immunodeficiency virus type 1

<400> SEQUENCE: 27

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu
65                  70                  75

<210> SEQ ID NO 28
<211> LENGTH: 75
<212> TYPE: PRT
<213> ORGANISM: Human immunodeficiency virus type 1

<400> SEQUENCE: 28

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
        35                  40                  45

Gly Leu Leu Glu Thr Ser Glu Gly Cys Lys Gln Ile Ile Gly Gln Leu
    50                  55                  60

Gln Pro Ser Ile Gln Thr Gly Ser Glu Glu Ile

```
                            65                  70                  75

<210> SEQ ID NO 29
<211> LENGTH: 75
<212> TYPE: PRT
<213> ORGANISM: Human immunodeficiency virus type 1

<400> SEQUENCE: 29

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Arg Gln Ile Ile Ser Gln Leu
    50                  55                  60

Gln Pro Ser Leu Lys Thr Gly Ser Glu Glu Leu
65                  70                  75

<210> SEQ ID NO 30
<211> LENGTH: 75
<212> TYPE: PRT
<213> ORGANISM: Human immunodeficiency virus type 1

<400> SEQUENCE: 30

Met Gly Ala Arg Ala Ser Val Leu Ser Gly Gly Lys Leu Asp Glu Trp
1               5                   10                  15

Glu Lys Ile Arg Leu Arg Pro Gly Gly Arg Lys Thr Tyr Lys Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Ala Gln Leu
    50                  55                  60

Gln Ser Ser Ile Gln Thr Gly Ser Glu Glu Ile
65                  70                  75

<210> SEQ ID NO 31
<211> LENGTH: 73
<212> TYPE: PRT
<213> ORGANISM: Human immunodeficiency virus type 1

<400> SEQUENCE: 31

Ala Arg Ala Ser Val Leu Ser Gly Gly Lys Leu Asp Glu Trp Glu Lys
1               5                   10                  15

Ile Gln Leu Arg Pro Gly Gly His Lys Arg Tyr Lys Leu Lys His Ile
            20                  25                  30

Val Trp Ala Ser Arg Glu Leu Glu Arg Phe Ala Ile Asn Pro Gly Leu
        35                  40                  45

Leu Glu Thr Ser Gly Gly Cys Arg Gln Ile Met Gly Gln Leu Gln Pro
    50                  55                  60

Ala Ile Gln Thr Gly Ser Glu Glu Leu
65                  70

<210> SEQ ID NO 32
<211> LENGTH: 73
<212> TYPE: PRT
<213> ORGANISM: Human immunodeficiency virus type 1

<400> SEQUENCE: 32
```

```
Ala Arg Ala Ser Val Leu Ser Gly Gly Lys Leu Asp Ala Trp Glu Lys
1               5                   10                  15

Ile Arg Leu Arg Pro Gly Gly Lys Arg Tyr Arg Leu Lys His Ile
            20                  25                  30

Val Trp Ala Ser Arg Glu Leu Glu Arg Phe Ala Leu Asn Pro Gly Leu
        35                  40                  45

Leu Glu Thr Ser Glu Gly Cys Lys Gln Ile Ile Ser Gln Leu Gln Pro
    50                  55                  60

Ser Leu Lys Thr Gly Ser Glu Glu Leu
65                  70

<210> SEQ ID NO 33
<211> LENGTH: 61
<212> TYPE: PRT
<213> ORGANISM: Human immunodeficiency virus type 1

<400> SEQUENCE: 33

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu
    50                  55                  60

<210> SEQ ID NO 34
<211> LENGTH: 61
<212> TYPE: PRT
<213> ORGANISM: Human immunodeficiency virus type 1

<400> SEQUENCE: 34

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
        35                  40                  45

Gly Leu Leu Glu Thr Ser Glu Gly Cys Lys Gln Ile Ile
    50                  55                  60

<210> SEQ ID NO 35
<211> LENGTH: 61
<212> TYPE: PRT
<213> ORGANISM: Human immunodeficiency virus type 1

<400> SEQUENCE: 35

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Arg Gln Ile Ile
    50                  55                  60

<210> SEQ ID NO 36
<211> LENGTH: 61
<212> TYPE: PRT
```

<213> ORGANISM: Human immunodeficiency virus type 1

<400> SEQUENCE: 36

Met Gly Ala Arg Ala Ser Val Leu Ser Gly Gly Lys Leu Asp Glu Trp
1               5                   10                  15

Glu Lys Ile Arg Leu Arg Pro Gly Gly Arg Lys Thr Tyr Lys Leu Lys
                20                  25                  30

His Ile Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile
        50                  55                  60

<210> SEQ ID NO 37
<211> LENGTH: 59
<212> TYPE: PRT
<213> ORGANISM: Human immunodeficiency virus type 1

<400> SEQUENCE: 37

Ala Arg Ala Ser Val Leu Ser Gly Gly Lys Leu Asp Glu Trp Glu Lys
1               5                   10                  15

Ile Gln Leu Arg Pro Gly Gly His Lys Arg Tyr Lys Leu Lys His Ile
                20                  25                  30

Val Trp Ala Ser Arg Glu Leu Glu Arg Phe Ala Ile Asn Pro Gly Leu
            35                  40                  45

Leu Glu Thr Ser Gly Gly Cys Arg Gln Ile Met
        50                  55

<210> SEQ ID NO 38
<211> LENGTH: 59
<212> TYPE: PRT
<213> ORGANISM: Human immunodeficiency virus type 1

<400> SEQUENCE: 38

Ala Arg Ala Ser Val Leu Ser Gly Gly Lys Leu Asp Ala Trp Glu Lys
1               5                   10                  15

Ile Arg Leu Arg Pro Gly Gly Arg Lys Arg Tyr Arg Leu Lys His Ile
                20                  25                  30

Val Trp Ala Ser Arg Glu Leu Glu Arg Phe Ala Leu Asn Pro Gly Leu
            35                  40                  45

Leu Glu Thr Ser Glu Gly Cys Lys Gln Ile Ile
        50                  55

<210> SEQ ID NO 39
<211> LENGTH: 61
<212> TYPE: PRT
<213> ORGANISM: Human immunodeficiency virus type 1

<400> SEQUENCE: 39

Met Gly Ala Arg Ala Ser Val Leu Ser Gly Gly Arg Leu Asp Ala Trp
1               5                   10                  15

Glu Lys Ile Arg Leu Arg Pro Gly Gly Lys Lys Lys Tyr Arg Met Lys
                20                  25                  30

His Leu Val Trp Ala Ser Arg Glu Leu Glu Arg Phe Ala Leu Asn Pro
            35                  40                  45

Gly Leu Leu Glu Thr Ala Glu Gly Cys Lys Gln Leu Met
        50                  55                  60

<210> SEQ ID NO 40
<211> LENGTH: 61

```
<212> TYPE: PRT
<213> ORGANISM: Human immunodeficiency virus type 1
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 40

Met Gly Ala Arg Ala Ser Val Leu Ser Gly Gly Lys Leu Asp Ser Trp
1               5                   10                  15

Glu Lys Ile Arg Leu Arg Pro Gly Gly Lys Lys Lys Tyr Arg Met Lys
                20                  25                  30

His Leu Val Trp Ala Ser Arg Glu Met Glu Arg Phe Ala Leu Asn Pro
            35                  40                  45

Asp Leu Leu Glu Thr Xaa Glu Gly Cys Gln Gln Ile Xaa
        50                  55                  60

<210> SEQ ID NO 41
<211> LENGTH: 59
<212> TYPE: PRT
<213> ORGANISM: Human immunodeficiency virus type 1

<400> SEQUENCE: 41

Ala Arg Ala Ser Val Leu Ser Gly Gly Lys Leu Asp Ala Trp Glu Lys
1               5                   10                  15

Ile Arg Leu Arg Pro Gly Gly Lys Lys Lys Tyr Arg Ile Lys His Leu
                20                  25                  30

Val Trp Ala Ser Arg Glu Leu Glu Arg Phe Ala Leu Asn Pro Gly Leu
            35                  40                  45

Leu Glu Thr Ala Glu Gly Cys Gln Gln Ile Met
        50                  55

<210> SEQ ID NO 42
<211> LENGTH: 61
<212> TYPE: PRT
<213> ORGANISM: Human immunodeficiency virus type 1

<400> SEQUENCE: 42

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Arg Tyr Arg Met Lys
                20                  25                  30

His Leu Val Trp Ala Ser Arg Glu Leu Asp Arg Phe Ala Leu Asn Pro
            35                  40                  45

Gly Leu Leu Glu Thr Ala Glu Gly Cys Gln Lys Ile Met
        50                  55                  60

<210> SEQ ID NO 43
<211> LENGTH: 61
<212> TYPE: PRT
<213> ORGANISM: Human immunodeficiency virus type 1

<400> SEQUENCE: 43

Met Gly Ala Arg Ala Ser Val Leu Thr Gly Gly Lys Leu Asp Ala Trp
1               5                   10                  15

Glu Lys Ile Arg Leu Arg Pro Gly Gly Arg Lys Ser Tyr Lys Ile Lys
                20                  25                  30
```

His Leu Val Trp Ala Ser Arg Glu Leu Glu Arg Phe Ala Leu Asn Pro
        35                  40                  45

Asp Leu Leu Glu Thr Ala Glu Gly Cys Gln Gln Ile Met
    50                  55                  60

<210> SEQ ID NO 44
<211> LENGTH: 61
<212> TYPE: PRT
<213> ORGANISM: Human immunodeficiency virus type 1

<400> SEQUENCE: 44

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Leu Lys
            20                  25                  30

His Leu Val Trp Ala Ser Arg Glu Leu Asp Arg Phe Ala Leu Asn Pro
        35                  40                  45

Ser Leu Leu Glu Thr Ser Glu Gly Cys Gln Gln Ile Ile
    50                  55                  60

<210> SEQ ID NO 45
<211> LENGTH: 61
<212> TYPE: PRT
<213> ORGANISM: Human immunodeficiency virus type 1

<400> SEQUENCE: 45

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Arg Met Lys
            20                  25                  30

His Leu Val Trp Ala Ser Arg Glu Leu Asp Arg Phe Ala Leu Asn Pro
        35                  40                  45

Gly Leu Leu Glu Thr Ala Glu Gly Cys Gln Gln Ile Leu
    50                  55                  60

<210> SEQ ID NO 46
<211> LENGTH: 61
<212> TYPE: PRT
<213> ORGANISM: Human immunodeficiency virus type 1
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 46

Met Gly Ala Arg Ala Ser Ile Leu Ser Gly Gly Arg Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Xaa Arg Phe Ala Leu Asn Pro
        35                  40                  45

Xaa Leu Leu Glu Ser Ala Glu Gly Cys Gln Gln Ile Met
    50                  55                  60

<210> SEQ ID NO 47
<211> LENGTH: 59
<212> TYPE: PRT
<213> ORGANISM: Human immunodeficiency virus type 1

<400> SEQUENCE: 47

Ala Arg Ala Ser Val Leu Ser Gly Gly Lys Leu Asp Ala Trp Glu Lys
1               5                   10                  15

Ile Gln Leu Arg Pro Gly Gly Lys Lys Lys Tyr Arg Leu Lys His Leu
            20                  25                  30

Val Trp Ala Ser Arg Glu Leu Glu Arg Phe Ala Leu Asn Pro Asp Leu
        35                  40                  45

Leu Glu Thr Ser Glu Gly Cys Gln Gln Ile Ile
    50                  55

<210> SEQ ID NO 48
<211> LENGTH: 59
<212> TYPE: PRT
<213> ORGANISM: Human immunodeficiency virus type 1

<400> SEQUENCE: 48

Ala Arg Ala Ser Val Leu Ser Gly Gly Lys Leu Asp Ser Trp Glu Lys
1               5                   10                  15

Ile Arg Leu Arg Pro Gly Gly Lys Lys Lys Tyr Arg Leu Lys His Leu
            20                  25                  30

Val Trp Ala Ser Arg Glu Leu Glu Arg Phe Ala Leu Asn Pro Ser Leu
        35                  40                  45

Leu Glu Thr Ala Glu Gly Cys Gln Gln Ile Met
    50                  55

<210> SEQ ID NO 49
<211> LENGTH: 61
<212> TYPE: PRT
<213> ORGANISM: Human immunodeficiency virus type 1

<400> SEQUENCE: 49

Met Gly Ala Arg Ala Ser Val Leu Arg Gly Glu Lys Leu Asp Thr Trp
1               5                   10                  15

Glu Arg Ile Arg Leu Arg Pro Gly Gly Lys Lys Lys Tyr Met Met Lys
            20                  25                  30

His Leu Val Trp Ala Ser Arg Glu Leu Glu Arg Phe Ala Leu Ala Pro
        35                  40                  45

Gly Leu Leu Glu Thr Ala Glu Gly Cys Arg Gln Ile Ile
    50                  55                  60

<210> SEQ ID NO 50
<211> LENGTH: 61
<212> TYPE: PRT
<213> ORGANISM: Human immunodeficiency virus type 1

<400> SEQUENCE: 50

Met Gly Ala Arg Ala Ser Ile Leu Arg Gly Gly Lys Leu Asp Ala Trp
1               5                   10                  15

Glu Lys Ile Gln Leu Arg Pro Gly Gly Lys Lys Arg Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Arg Gln Ile Ile
    50                  55                  60

<210> SEQ ID NO 51
<211> LENGTH: 61
<212> TYPE: PRT

<213> ORGANISM: Human immunodeficiency virus type 1

<400> SEQUENCE: 51

Met Gly Ala Arg Ala Ser Val Leu Arg Gly Glu Lys Leu Asp Thr Trp
1               5                   10                  15

Glu Arg Ile Arg Leu Arg Pro Gly Gly Lys Lys Lys Tyr Met Met Lys
            20                  25                  30

His Leu Val Trp Ala Ser Arg Glu Leu Glu Arg Phe Ala Leu Ala Pro
        35                  40                  45

Gly Leu Leu Glu Thr Ala Glu Gly Cys Arg Gln Ile Ile
    50                  55                  60

<210> SEQ ID NO 52
<211> LENGTH: 61
<212> TYPE: PRT
<213> ORGANISM: Human immunodeficiency virus type 1

<400> SEQUENCE: 52

Met Gly Ala Arg Ala Ser Ile Leu Arg Gly Gly Lys Leu Asp Ala Trp
1               5                   10                  15

Glu Lys Ile Gln Leu Arg Pro Gly Gly Lys Lys Arg Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Arg Gln Ile Ile
    50                  55                  60

<210> SEQ ID NO 53
<211> LENGTH: 59
<212> TYPE: PRT
<213> ORGANISM: Human immunodeficiency virus type 1

<400> SEQUENCE: 53

Ala Arg Ala Ser Ile Leu Arg Gly Gly Gln Leu Asp Arg Trp Glu Lys
1               5                   10                  15

Ile Arg Leu Arg Pro Gly Gly Lys Lys His Tyr Met Leu Lys His Leu
            20                  25                  30

Val Trp Ala Ser Arg Glu Leu Glu Arg Phe Val Leu Asn Pro Gly Leu
        35                  40                  45

Leu Glu Thr Ala Glu Gly Cys Lys Gln Ile Met
    50                  55

<210> SEQ ID NO 54
<211> LENGTH: 61
<212> TYPE: PRT
<213> ORGANISM: Human immunodeficiency virus type 1

<400> SEQUENCE: 54

Met Gly Ala Arg Ala Ser Ile Leu Thr Gly Glu Lys Leu Asp Ala Trp
1               5                   10                  15

Glu Lys Ile Arg Leu Arg Pro Gly Gly Lys Lys Lys Tyr Met Ile Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Gln Gln Ile Ile
    50                  55                  60

<210> SEQ ID NO 55
<211> LENGTH: 61

<212> TYPE: PRT
<213> ORGANISM: Human immunodeficiency virus type 1

<400> SEQUENCE: 55

Met Gly Ala Arg Ala Ser Ile Leu Ser Gly Gly Lys Leu Asp Ala Trp
1               5                   10                  15

Glu Lys Ile Arg Leu Arg Pro Gly Gly Arg Lys Lys Tyr Arg Met Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Gln Gln Leu Ile
    50                  55                  60

<210> SEQ ID NO 56
<211> LENGTH: 61
<212> TYPE: PRT
<213> ORGANISM: Human immunodeficiency virus type 1

<400> SEQUENCE: 56

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Gln Leu Lys
            20                  25                  30

His Val Val Trp Ala Ser Arg Glu Leu Glu Arg Phe Ala Leu Asn Pro
        35                  40                  45

Gly Leu Leu Glu Thr Ala Glu Gly Cys Gln Gln Ile Ile
    50                  55                  60

<210> SEQ ID NO 57
<211> LENGTH: 61
<212> TYPE: PRT
<213> ORGANISM: Human immunodeficiency virus type 1

<400> SEQUENCE: 57

Met Gly Ala Arg Ala Ser Ile Leu Thr Gly Gly Lys Leu Asp Ala Trp
1               5                   10                  15

Glu Lys Ile Arg Leu Arg Pro Gly Gly Lys Lys Lys Tyr Met Ile Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Gln Gln Ile Ile
    50                  55                  60

<210> SEQ ID NO 58
<211> LENGTH: 61
<212> TYPE: PRT
<213> ORGANISM: Human immunodeficiency virus type 1

<400> SEQUENCE: 58

Met Gly Ala Arg Ala Ser Val Leu Ser Gly Gly Lys Leu Asp Trp
1               5                   10                  15

Glu Lys Ile Arg Leu Arg Pro Gly Gly Lys Lys Gln Tyr Lys Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Arg Lys Ile Ile
    50                  55                  60

<210> SEQ ID NO 59

```
<211> LENGTH: 61
<212> TYPE: PRT
<213> ORGANISM: Human immunodeficiency virus type 1

<400> SEQUENCE: 59

Met Gly Ala Arg Ala Ser Val Leu Ser Gly Gly Lys Leu Asp Ala Trp
1               5                   10                  15

Glu Arg Ile Arg Leu Arg Pro Gly Gly Lys Lys Lys Tyr Arg Met Lys
            20                  25                  30

His Leu Ile Trp Ala Gly Arg Glu Leu Asp Arg Phe Ala Leu Asp Pro
        35                  40                  45

Gly Leu Leu Glu Thr Ser Glu Gly Cys Arg Lys Ile Ile
    50                  55                  60

<210> SEQ ID NO 60
<211> LENGTH: 61
<212> TYPE: PRT
<213> ORGANISM: Human immunodeficiency virus type 1

<400> SEQUENCE: 60

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Met Lys
            20                  25                  30

His Leu Ile Trp Ala Ser Arg Glu Leu Glu Arg Phe Ala Leu Asp Ser
        35                  40                  45

Gly Leu Leu Glu Thr Thr Glu Gly Cys Arg Lys Ile Ile
    50                  55                  60

<210> SEQ ID NO 61
<211> LENGTH: 61
<212> TYPE: PRT
<213> ORGANISM: Human immunodeficiency virus type 1

<400> SEQUENCE: 61

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Lys Met Lys
            20                  25                  30

His Leu Ile Trp Ala Ser Arg Glu Leu Glu Arg Phe Ala Leu Asp Pro
        35                  40                  45

Gly Leu Leu Glu Thr Ser Glu Gly Cys Arg Lys Ile Ile
    50                  55                  60

<210> SEQ ID NO 62
<211> LENGTH: 38
<212> TYPE: PRT
<213> ORGANISM: Human immunodeficiency virus type 1

<400> SEQUENCE: 62

Gly Gly Lys Lys Lys Tyr Arg Leu Lys His Leu Val Trp Ala Ser Arg
1               5                   10                  15

Glu Leu Glu Arg Phe Ala Leu Asn Pro Gly Leu Leu Glu Thr Thr Glu
            20                  25                  30

Gly Cys Lys Gln Ile Ile
        35

<210> SEQ ID NO 63
<211> LENGTH: 61
<212> TYPE: PRT
```

<213> ORGANISM: Human immunodeficiency virus type 1

<400> SEQUENCE: 63

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Arg Leu Lys
            20                  25                  30

His Leu Val Trp Ala Ser Arg Glu Leu Glu Arg Phe Ala Leu Asn Pro
        35                  40                  45

Asp Leu Leu Glu Thr Ala Asp Gly Cys Gln Gln Ile Leu
    50                  55                  60

<210> SEQ ID NO 64
<211> LENGTH: 61
<212> TYPE: PRT
<213> ORGANISM: Human immunodeficiency virus type 1

<400> SEQUENCE: 64

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
        35                  40                  45

Asp Leu Leu Asp Thr Ala Glu Gly Cys Leu Gln Leu Ile
    50                  55                  60

<210> SEQ ID NO 65
<211> LENGTH: 61
<212> TYPE: PRT
<213> ORGANISM: Human immunodeficiency virus type 1

<400> SEQUENCE: 65

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
        35                  40                  45

Gly Leu Leu Glu Thr Pro Glu Gly Cys Leu Gln Ile Ile
    50                  55                  60

<210> SEQ ID NO 66
<211> LENGTH: 61
<212> TYPE: PRT
<213> ORGANISM: Human immunodeficiency virus type 1
<220> FEATURE:
<221> NAME/KEY: misc_feature
<222> LOCATION: (61)..(61)
<223> OTHER INFORMATION: Xaa can be any naturally occurring amino acid

<400> SEQUENCE: 66

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Asp Arg Phe Ala Leu Asn Pro
        35                  40                  45

Asp Leu Leu Glu Thr Ala Asp Gly Cys Leu Lys Ile Xaa
    50                  55                  60

```
<210> SEQ ID NO 67
<211> LENGTH: 61
<212> TYPE: PRT
<213> ORGANISM: Human immunodeficiency virus type 1

<400> SEQUENCE: 67

Met Gly Ala Arg Ala Ser Ile Leu Ser Gly Gly Lys Leu Asp Asp Trp
1               5                   10                  15

Glu Lys Ile Arg Leu Arg Pro Gly Gly Lys Lys Gln Tyr Arg Ile Lys
            20                  25                  30

His Leu Val Trp Ala Ser Arg Glu Leu Asp Arg Phe Ala Leu Asn Pro
        35                  40                  45

Gly Leu Leu Glu Ser Ala Lys Gly Cys Gln Gln Ile Leu
    50                  55                  60
```